(12) United States Patent
So et al.

(10) Patent No.: US 12,257,230 B2
(45) Date of Patent: *Mar. 25, 2025

(54) COMPOSITION COMPRISING NAPHTHOQUINONE-BASED COMPOUND AS ACTIVE INGREDIENT, FOR PREVENTING OR AMELIORATING FATIGUE, CACHEXIA, PAIN, COGNITIVE DECLINE AND HEMATOPOIETIC STEM CELL REDUCTION WHICH ARE SIDE EFFECTS RELATED TO ANTICANCER DRUG TREATMENT

(71) Applicant: NADIANBIO LTD., Iksan-si (KR)

(72) Inventors: Hong Seob So, Iksan-si (KR); Hyung-Jin Kim, Iksan-si (KR); Gi-Su Oh, Iksan-si (KR); Seunghoon Lee, Iksan-si (KR); Dipendra Khadka, Iksan-si (KR)

(73) Assignee: NADIANBIO Ltd., Iksan-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/097,028

(22) PCT Filed: Apr. 28, 2017

(86) PCT No.: PCT/KR2017/004600
§ 371 (c)(1),
(2) Date: Oct. 26, 2018

(87) PCT Pub. No.: WO2017/188791
PCT Pub. Date: Nov. 2, 2017

(65) Prior Publication Data
US 2019/0083453 A1 Mar. 21, 2019

(30) Foreign Application Priority Data
Apr. 29, 2016 (KR) .................. 10-2016-0053171

(51) Int. Cl.
A61K 31/352 (2006.01)
A61K 31/337 (2006.01)
(Continued)

(52) U.S. Cl.
CPC .......... *A61K 31/352* (2013.01); *A61K 31/337* (2013.01); *A61K 31/343* (2013.01);
(Continued)

(58) Field of Classification Search
CPC .. A61K 31/337; A61K 31/343; A61K 31/352; A61K 31/65; A61K 31/675;
(Continued)

(56) References Cited

U.S. PATENT DOCUMENTS 6,245,807 B1 * 6/2001 Pardee ................. A61K 31/352
514/454
7,435,725 B2 10/2008 Rosenbloom
(Continued)

FOREIGN PATENT DOCUMENTS

KR 10-2014-0058734 A 5/2014

OTHER PUBLICATIONS

Yan (Paclitaxel induces acute pain via directly activating toll like receptor 4, Molecular Pain (2015) 11:10).*
(Continued)

*Primary Examiner* — Jeffrey S Lundgren
*Assistant Examiner* — Anthony Joseph Seitz
(74) *Attorney, Agent, or Firm* — Sughrue Mion, PLLC

(57) ABSTRACT

The present invention relates to a composition comprising a naphthoquinone-based compound as an active ingredient, for preventing or ameliorating fatigue, cachexia, pain, cognitive decline, and hematopoietic stem cell reduction which are side effects related to anticancer drug treatment. Specifically, it has been confirmed that the naphthoquinone-based compounds, dunnione and β-lapachone, reduce the
(Continued)

secretion and production of inflammatory cytokines which are increased by the anticancer drug treatment, and prevent fatigue, cachexia, cognitive decline, and hematopoietic stem cell reduction which are side effects associated with anticancer drug treatment, and thus the dunnione and β-lapachone compounds, pharmaceutically acceptable salts, prodrugs, solvates or isomers thereof can be effectively used as a pharmaceutical composition for preventing or ameliorating any one or more side effects related to anticancer drug treatment selected from the group consisting of fatigue, cachexia, pain, cognitive decline, and hematopoietic stem cell reduction.

5 Claims, 23 Drawing Sheets
(2 of 23 Drawing Sheet(s) Filed in Color)

(51) Int. Cl.
| | |
|---|---|
| A61K 31/343 | (2006.01) |
| A61K 31/65 | (2006.01) |
| A61K 31/675 | (2006.01) |
| A61K 45/06 | (2006.01) |
| A61P 3/00 | (2006.01) |
| A61P 7/00 | (2006.01) |
| A61P 21/00 | (2006.01) |
| A61P 25/00 | (2006.01) |
| A61P 29/00 | (2006.01) |
| A61P 35/00 | (2006.01) |

(52) U.S. Cl.
CPC ............ *A61K 31/65* (2013.01); *A61K 31/675* (2013.01); *A61K 45/06* (2013.01); *A61P 3/00* (2018.01); *A61P 7/00* (2018.01); *A61P 21/00* (2018.01); *A61P 25/00* (2018.01); *A61P 29/00* (2018.01); *A61P 35/00* (2018.01)

(58) Field of Classification Search
CPC .......... A61K 45/06; A61P 21/00; A61P 25/00; A61P 29/00; A61P 35/00; A61P 3/00; A61P 7/00
See application file for complete search history.

(56) References Cited

U.S. PATENT DOCUMENTS

| | | | | |
|---|---|---|---|---|
| 7,435,726 | B2* | 10/2008 | Zeldis | A61K 31/454 514/183 |
| 7,649,013 | B2* | 1/2010 | Li | A61K 31/352 514/454 |
| 8,614,228 | B2 | 12/2013 | Ashwell et al. | |
| 2023/0372286 | A1* | 11/2023 | So | A61K 31/337 |

OTHER PUBLICATIONS

Boussios (Systemic treatment-induced gastrointestinal toxicity: incidence, clinical presentation and management, Annals of Gastroenterology (2012) 25, 106-118).*
Mendoza (Adriamycin-Cyclophosphamide (AC) followed by Paclitaxel-Cisplatin (PC). A highly active neoadjuvant regimen in locally advanced breast cancer, 24th Annual Meeting of the National Cancer Institute of Mexico Mexico City, Mexico, 2007, 1471-2407-7-S1-A1.fm (nih.gov)).*
Jong (Prevalence and course of fatigue in breast cancer patients receiving adjuvant chemotherapy, Annals of Oncology 15, 896-905, 2004).*
Hudis et al., J Clin Oncol. Jan. 1999;17(1):93-100 (Year: 1999).*
Sun et al., (1998) Scandinavian Journal of Gastroenterology, 33:4, 415-422 (Year: 1998).*
Hruban et al., Cancer. May 15, 1989;63(10):1944-50 (Year: 1989).*
Luo et al., International Immunopharmacology, vol. 119, 2023, 110244 ISSN 1567-5769 (Year: 2023).*
Pandit et al., Biochemical and Biophysical Research Communications, vol. 467, Issue 4, 2015, pp. 697-703 (Year: 2015).*
M.M. Sitônio et al., "Anti-inflammatory and anti-arthritic activities of 3,4-dihydro-2,2-dimethyl-2H-naphthol[1,2-b]pyran-5,6-dione (β-lapachone)" Inflammation Research, 2012, pp. 107-113.
Dongsun Park et al., A Dunnione Compound MB12662 improves Cisplatin-Induced Tissue Injury and Emesis Biomolecule & Therapeutics, vol. 23 No. 5, 2015, pp. 449-457.
Dong-oh Moon et al., "Anti-inflammatory effects of (α-lapachone in lipopolysaccharide-stimulated BV2 microglia" International Immunopharmacology, vol. 7, 2007, pp. 506-514, (9 Pages total).
European Patent Office, Communication dated Apr. 2, 2019 issued in counterpart application No. 17789975.4.
Kurzrock "The Role of Cytokines in Cancer-Related Fatigue" *Cancer* Supplement 92(6):1684-1688 (2001).
Choi et al. "Effects of β-lapachone on the Production of Inflammatory Cytokines in Mice" *Cancer Prevention Research* 16(2):155-160 (2011).
Suzuki et al. "Cancer cachexia—pathophysiology and management" J. Gastroenterol 48:574-594 (2013).
Cheung et al. "Association of proinflammatory cytokines and chemotherapy-associated cognitive impairment in breast cancer patients: a multi-centered, prospective, cohort study" *Annals of Oncology* 26:1446-1451 (2015).
Lee et al. "β-Lapachone suppresses neuroinflammation by modulating the expression of cytokines and matrix metalloproteinases in activated microgilia" *Journal of Neuroinflammation* 12:133 (2015).
Pandit et al. "Dunnione ameliorates cisplatin-induced small intestinal damage by modulating NAD metabolism" *Biochemical and Biophysical Research Communications* 467:697-703 (2015).
Vendrell et al. "Treatment of Cancer Pain by Targeting Cytokines" *Mediators of Inflammation* 11 pages (2015) http://dx.doi.org/10.1155/2015/984570.
Josep M. Argilés et al., "The Role of Cytokines in Cancer Cachexia", Med. Res. Rev., vol. 19, No. 3, pp. 223-248, 1999, 27 pages total.
Julienne E. Bower, Ph.D. et al., "Inflammation and cancer-related fatigue: Mechanisms, contributing factors, and treatment implications", Brain, Behavior and Immunity, vol. 30, Mar. 2013, pp. 1-21.
Carolina Panis et al., "Cytokines as Mediators of Pain-Related Process in Breast Cancer", Mediators of Inflammation, vol. 2015, Oct. 25, 2015, pp. 1-6.
Yin Ting Cheung et al., "Cytokines as Mediators of Chemotherapy-Associated Cognitive Changes: Current Evidence, Limitations and Directions for Future Research", PLoS ONE, vol. 8, No. 12, e81234, Dec. 2013, pp. 1-12.
Cheng C Zhang et al., "Cytokines regulating hematopoietic stem cell function", Current Opinion In Hematology, vol. 15, No. 4, Jul. 2008, pp. 1-8.

* cited by examiner

COMPOSITION COMPRISING NAPHTHOQUINONE-BASED COMPOUND AS ACTIVE INGREDIENT, FOR PREVENTING OR AMELIORATING FATIGUE, CACHEXIA, PAIN, COGNITIVE DECLINE AND HEMATOPOIETIC STEM CELL REDUCTION WHICH ARE SIDE EFFECTS RELATED TO ANTICANCER DRUG TREATMENT

CROSS REFERENCE TO RELATED APPLICATIONS

This is the U.S. National Stage of International Application No. PCT/KR2017/004600, filed Apr. 28, 2017, which in turn claims the benefit of Korean Patent Application No. 10-2016-0053171, filed Apr. 29, 2016, both of which applications are herein incorporated in their entirety.

BACKGROUND OF THE INVENTION

1. Field of the Invention

The present invention relates to a pharmaceutical composition comprising a naphthoquinone-based compound, a prodrug, a solvate or an isomer thereof as an active ingredient, for preventing or ameliorating any one or more side effects related to anticancer drug treatment selected from the group consisting of fatigue, cachexia, pain, cognitive decline, and hematopoietic stem cell reduction.

2. Description of the Related Art

Cancer is one of the critical diseases threatening human health and life, which is in an ever-increasing trend. The treatment methods of cancer include surgical operation, radio-therapy, bio-therapy, and chemo-therapy. Among these methods, chemo-therapy is performed with anticancer agents, which are involved in the metabolic pathway of cancer cells to interact directly with DNA, precisely to block the replication, transcription and translation of DNA, to interrupt the synthesis of nucleic acid precursors, or to inhibit cell division, causing cytotoxicity. In cancer patients, inflammatory cytokines are secreted from cancer tissue itself and as a result metabolic rate increases and thus energy demand increases. In the meantime, cancer patients lose nutritional intake due to anorexia, resulting in weight loss and deterioration of nutritional status (Van Cutsem et al. 2005). Anticancer chemotherapy, a major cancer treatment method, increases the production of inflammatory cytokines, which causes a variety of side effects. The over-production and excessive secretion of cytokines are closely related to such side effects caused by anticancer drug treatment as fatigue, cachexia, pain and cognitive decline, according to the previous reports (Wood et al. 2006; Meriggi F. 2014; Madeddu et al. 2015; Cheung et al. 2013; Cheung et al. 2015). Therefore, the regulation of cytokine can be a way to increase the effectiveness of anticancer chemo-therapy while minimizing fatigue, cachexia, pain and cognitive decline caused by chemo-therapy. Under the inflammation reaction condition, the hematopoietic stem cell differentiation is accelerated, which reduces self-replication ability and eventually depletes hematopoietic stem cells (King et al. 2011). Therefore, the regulation of cytokine can be a method to prevent or improve side effects of anticancer drugs while minimizing the reduction of hematopoietic stem cells caused by anticancer drug treatment. These cytokines are polypeptides that affect cellular functions and regulate the interaction between cells involved in immune, inflammatory or hematopoietic responses, and include monokines (produced and secreted by mononuclear cells such as macrophages and monocytes) and lymphocytes (produced and secreted by lymphocytes). Interleukin-1 (IL-1), interleukin-6 (IL-6), interleukin-17 (IL-17), and tumor necrosis factors (TNFs including TNF-alpha and TNF-beta) are examples of cytokines. It has been confirmed that cytokines are involved in various reactions particularly in immune system and inflammation response (Stark et al. 2015; Kim et al. 2016; Lopez Gonzalez I et al. 2016). However, excessive or uncontrolled production and secretion of cytokines causes a deficiency of immunoregulatory function, by which they mediate or aggravate various diseases and symptoms (Conti et al. 2016; Leitner et al. 2016; Ridker P M. 2016; Stark et al. 2015). Cytokines are produced in various types of cells and play an important role in controlling the host immune response and are involved in a variety of pathologies as well (Fang et al. 2015; Ezeoke et al. 2015; Inacio Pinto et al. 2015).

Role of Cytokine in Cancer-Related Fatigue (CRF)

One of the side effects most frequently observed in the middle of or after the treatment of cancer is cancer-related fatigue. According to National Comprehensive Cancer Network (NCCN), cancer-related fatigue is defined by "a subjective sensation of tiredness and discomfort due to cancer and anticancer treatment that is painful and persistent, but is not related to recent activity and interrupts ordinary functions" (National Comprehensive Cancer Network. 2016). Cancer-related fatigue (CRF) can be distinguished from general fatigue in that it is not relieved by rest and is not triggered primarily by physical activity. CRF of cancer patients is very serious, chronic and painful, which is not relieved by rest. Many studies have shown that CRF, among many cancer-related side effects, is the most negative effect on the quality of cancer patient's life with limiting daily life (Cleeland et al. 2003; Curt et al. 2000; Tsai et al. 2006). The exact cause of CRF is not well known, but it is known that cancer itself or the process of cancer-treatment is associated with the development of CRF. In particular, the chemotherapy based on nearly all anticancer agents is known to increase the incidence of CRF. The incidence of cancer-related fatigue (CRF) in the course of cancer-treatment varies with the treatment method and treatment period, but almost all cancer patients experience CRF (Weis J. 2011). That is, the incidence rate of cancer-related fatigue (CRF) in cancer patients who are not receiving chemo-therapy is about 70-80%, and the incidence rate of CRF in cancer patients receiving chemo-therapy is higher than that (Hofman et al. 2007). Cancer patients who have had bone marrow transplantation and chemotherapy feel CRF worse than those patients who have treated with adjuvant chemo-therapy without bone marrow transplantation. Cancer patients treated with adjuvant chemo-therapy experience CRF more frequently and seriously than those patients treated with radio-therapy (Manir et al. 2012). As explained, cancer-related fatigue (CRF) requires excessive rest, and thus causes muscle weakness, muscle atrophy, muscle weakness and cardiopulmonary dysfunction, making basic everyday life of cancer patients more devastated (Glaus A. 1998; Winningham et al. 1994).

Drug therapies for cancer-related fatigue (CRF) are largely to treat symptoms instead of targeting a cause and cannot solve the problems of decreased physical strength and decline in muscle mass and muscle function observed in the course of cancer treatment.

Currently, modafinil is undergoing clinical trials as a therapeutic agent for cancer-related fatigue (CRF) of patients with metastatic breast cancer and prostate cancer in combination with docetaxel-based chemotherapy (Hovey et al. 2014). The primary pharmacological activity of modafinil is to increase awareness. It was confirmed in the cancer-related fatigue animal model that modafinil accelerated awareness (Touret et al. 1995; Edgar and Seidel, 1997; Shelton et al. 1995; Hernant et al. 1991; Panckeri et al. 1996; Shelton et al. 1995).

Meanwhile, attempts have been made to relieve CRF by proper therapeutic exercise in the course of cancer treatment (Tian et al. 2015; Dash et al. 2016).

It is strongly suggested that the cause of cancer-related fatigue (CRF) observed in cancer patients receiving chemotherapy can be the increased activity of pro-inflammatory cytokines and the decreased activity of orexin along with the decrease of intramuscular glycogen synthesis. Therefore, it is requested to develop a novel drug based on the mechanism of CRF induction (Ryan et al. 2007; Barsevick et al. 2010; Weymann et al. 2014).

Inflammatory cytokines such as IL-10, IL-6 and TNF-α are significantly increased during malignancy or in the course of its treatment. According to the previous report, the mechanism of inflammatory cytokines involved in causing fatigue is closely related to mal-functioning of the suprachiasmatic nucleus (SCN) (Neefjes et al. 2013). The suprachiasmatic nucleus (SCN) is located just in front of the hypothalamus of the brain, just above the intersection of the optic nerves. To regulate physiological cycle, the activity of nerve and hormone is controlled through neurons in order to induce and regulate various functions in 24 hour cycle of human being. In particular, the hormones cortisol and serotonin activate glucocorticoid receptors and HT-1a receptors respectively, resulting in the regulation of the function of the suprachiasmatic nucleus (SCN) like the regulation of physiological cycle, etc. In the meantime, the inflammatory cytokines IL-10, IL-6 and TNF-α generated in malignancy or in the course of its treatment cause mal-functioning of the suprachiasmatic nucleus (SCN) by interrupting the normal hormone synthesis or function, resulting in fatigue condition.

Orexin is a neurohormone secreted by orexin neurons in the hypothalamus. Orexin is known as a hormone that awakens consciousness and enhances attention. It has been recently reported that the inflammatory response in the hypothalamus reduces the activity of orexin neurons in the hypothalamus and thereby the decrease of orexin production/release causes cancer-related fatigue observed in the course of cancer treatment by chemo-therapy (Weymann et al. 2014).

Therefore, the development of a drug that can inhibit the production or activity of inflammatory cytokines or increase the production of orexin to provides a sufficient possibility of using the drug for preventing or ameliorating fatigue, one of the side effects caused by anticancer drug treatment for malignancy.

Role of Inflammatory Cytokines in Cachexia

Along with fatigue, cachexia is a common symptom of cancer patients with advanced forms of cancer. This symptom can be aggravated as cancer progresses. About 50-80% of those patients with advanced forms of cancer experience cachexia. Incidence rate of cachexia varies from the type of cancer. In particular, 80% of total gastrointestinal cancer patients are experiencing cachexia as they are diagnosed with cancer, while the rate is comparatively low in lymphoma or breast cancer patients (Bruera E. 1997). Cachexia can be caused by cancer itself and also it can occur in the course of cancer treatment like chemo-therapy (Aoyagi et al. 2015; Braun et al. 2014).

Unlike simple fasting or anorexia, this symptom observed in cancer patients carries severe weight loss and skeletal muscle atrophy. Weight loss not only decreases quality of life but also shortens life expectancy. Previous studies showed that weight loss mediated cachexia was the direct cause of death in 10-20% of total cancer patients (Bruera E. 1997). Cachexia is associated with fatigue, loss of muscle strength and neurohormonal and biochemical abnormalities. The path physiological characteristics of cachexia are negative protein and energy imbalance induced by various combinations of reduced food intake and abnormal metabolism. Patients with solid tumors, colorectal cancer (CRC) and non-small cell lung cancer (NSCLC) exhibit a relatively high incidence of cachexia of approximately 28% and 34%, respectively (Kern et al. 1988; Lahdevirta et al. 1988). Cancer patients experiencing cachexia show low response to anticancer chemo-therapy and they experience more severe side effects (Slaviero et al. 2003).

Cachexia mediated weight loss and muscle atrophy (muscle weakness) destroy lifestyle and human relationship. It also affects patient's will or ability to fight cancer so that it has a negative effect on the recovery of those patients with advanced forms of cancer. To alleviate cachexia, therapeutic nutritional and endocrine therapy can be performed, which are though not as satisfactory as expected.

In particular, if cachexia is due to cancer, there is a serious disruption in the course of treatment, as the use of anticancer chemotherapy cannot be administered if cachexia progresses. Especially if cancer caused cachexia progresses, anticancer chemo-therapy cannot be continued, indicating the treatment process is disrupted or even failed. Any therapeutic effect for the relief of cachexia symptoms can rather exacerbate cancer and shorten the lifespan of cancer patient. Cachexia is attributed mostly to cancer, so that the administration of anticancer drugs can control cancer. However, in that case, other side effects of the drug can be overlapped and eventually cachexia is not improved at all but can be worsen (Nelson et al. 1994).

It was disclosed that cachectin known as a cachexia causing material was the same factor as TNF and such cytokines as interleukin (IL-1) or IL-6 play a same role to the material. Therefore, the over-expression of inflammatory was noted as a major cause of cachexia (Argiles et al. 2005; Lelbach et al. 2007). Anorexia cachexia, observed mainly in cancer patients, is developed when inflammatory cytokines such as TNF-α, IL-6 and IL-1B which are produced in normal tissues and cancer tissues are conjugated to their receptors to increase the activity of neurons expressing POMC (pro-opiomelanocortin) and at the same time to activate MC4R (melanocortin-4 receptor) by releasing α-MSH (α-melanocyte stimulating hormone). The activation of such receptors reduces appetite, increases energy consumption and increases the decomposition of lean mass. On the contrary, ghrelin stimulates GHSR-1a receptor and thus increases the expression and secretion of AgRP (agouti-related peptide) and neuropeptide-Y associated with appetite stimulation. It has been recently attempted to prevent and treat cachexia by using the agonist of GHSR-1a receptor or ghrelin (Mark D. DeBoer. 2011). Leptin is the most representative hormone that works on the hypothalamus to reduce food intake and to stimulate energy consumption, and accordingly causes weight loss. According to the previous reports, the expression of leptin increases in cachexia cases induced by chronic diseases such as chronic kidney disease and congestive heart failure, etc (Engineer et al. 2012). In particular, it was also reported that weight loss was caused not just by anorexia alone but chronic inflammation was more important reason of weight loss (Walsmith et al. 2002). Consistently with the studies above, not only weight loss but also muscle loss was observed in the adjuvant arthritis model of rats, wherein the expressions of TNF-α and IL-1ß genes and proteins were increased in the skeletal muscle. Weight loss and skeletal muscle weight loss caused by adjuvant arthritis in the rat model were more effectively prevented when TNF-α and IL-1B were suppressed simultaneously than when TNF-α alone was inhibited. Therefore, it was suggested that the combined work of TNF-α and IL-1B induced muscle loss to cause cachexia thereby (Walsmith et al. 2002).

In the meantime, the skeletal muscle weight loss and muscle wasting caused by inflammation response activate ubiquitin-proteasome proteolysis pathway and autophagic/lysosomal proteolysis pathway, by which muscle protein is decomposed (Zhao et al. 2007). In particular, the increase of ubiquitin ligases such as MAFbx/Atrogin-1 (muscle atrophy F-Box) and MuRF1 (muscle RING finger-1) and the up-regulations of autophage related genes such as Bnip3 are directly involved in the muscle protein decomposition. The inhibition of NF-kB which is an important transcription factor involved in the regulation of inflammatory cytokine expression can cause down-regulation of proteasome in the skeletal muscle (Wyke et al. 2004).

Therefore, the development of a drug that can inhibit the generation or function of inflammatory cytokines and thereby inhibit the ubiquitin-proteasome proteolysis pathway and autophagic/lysosomal proteolysis pathway provides a great possibility of using the drug for the prevention or amelioration of cachexia observed as a side effect in the course of anticancer drug treatment.

Role of Inflammatory Cytokines in Cancer-Related Pain

For the improvement of the quality of life of cancer patients and the therapeutic effect, pain control is an important part of cancer treatment. Cancer-related pain is caused by bone metastasis of cancer cells, nerve compression, vascular invasion, lymph and organ invasion, or vascular occlusion by cancer cells (Delaney et al. 2008; Vendrell et al. 2015; Laird et al. 2013). According to the previous report, 33-64% of patients with advanced cancer complained pain, and more than 50% of them were not properly treated in their pain (Mantyh et al. 2002; Teunissen et al. 2007). Cancer-related pain can be caused by primary cancer itself or by other parts of the body where the cancer has spread (metastasized). As a tumor grows, it can press nerves, bones, or other organs, which can cause pain. Cancer-related pain is one of the causes of sleep disturbance, which increases fatigue and causes both physical symptoms like loss of appetite and emotional symptoms like anxiety, etc (Cleeland C S. 1984; McGuire D B. 1987). At least 60% of those cancer patients complaining fatigue also experience severe pain, suggesting that fatigue and pain are closely related (Blesch et al. 1991; Haghighat et al. 2003; Hwang et al. 2003). It was also reported that severe pain in cancer patients with bone metastasis induced in the course of radio-therapy caused sleep disturbance, resulting in the increase of fatigue (Miaskowski et al. 1999).

The two major types of drugs used for the treatment of cancer-related pain are opioid analgesics and non-steroidal anti-inflammatory drugs (NSAID). These drugs are typically administered systemically. The systemic administration of opioids causes nausea, intestinal dysfunction, urinary retention, and pulmonary dysfunction.

According to the recent studies, cancer-related pain is induced not only by the physical consequences of cancer in the body but also by inflammatory cytokines (TNF-α, IL-6, IL-1β, IL-17, etc.) secreted from cancer cells (Laird et al. 2011; Zhang et al. 2007; Sommer et al. 2004). Cytokines are the representative materials mediating inflammatory response, which are known as the major cause of spinal cord injury and neuropathic pain and also known to play a certain role in the development and maintenance of chronic pain (Gaultier et al. 2008; Choi et al. 2010). Chemo-therapy performed for cancer treatment accompanies such side effect as anticancer agent-induced nerve pain. 30-90% of cancer patients who had been treated with taxane-based anticancer agents including paclitaxel and other combined anticancer agents experienced anticancer agent-induced nerve pain (Farquhar-Smith P. 2011; Polomano et al. 2001; Xiao et al. 2012). The anticancer agent-induced nerve pain is induced when the activation of NF-kB and MAPKs (ERK and p38) accelerates the production of inflammatory and neurotoxic cytokines (TNF-α, IL-1B, etc.) (Janes et al. 2014). Most anticancer agents pass through the blood-nerve-barrier and then bind to the dorsal root ganglia and peripheral axons to increase neurotoxicity (Wang et al. 2012). Some anticancer agents inhibit tubulin function and accordingly interrupt axon transport of nutrients and cause sensory nerve regression and release inflammatory cytokines (Mantyh et al. 2002).

The Blood-Brain Barrier is a membrane with a low permeability located between capillaries and brain tissue. It plays an important role in maintaining homeostasis in the central nervous system by adherent Junction and tight Junction between brain capillary endothelial cells (Brown et al. 2002). In such a pathological condition as inflammatory pain, impaired ion homeostasis and transport dysfunction are observed in the blood-brain-barrier (Huber et al. 2001). Blood inflammatory cytokines cause damage on the blood-brain-barrier, by which the amount of inflowing white blood cells and macrophages increases. Such immune cells increase the production of TNF-α and therefore make the inflammatory response in the brain tissue worse, further leading to brain damage (Keep et al. 2008). In the normal condition, TNF-α is strictly regulated, but when inflammation occurs in the brain, macrophages and microglia increase the activity and production of TNF-α (Gearing et al. 1994; Bethea J R et al. 1990). TNF-α is a major mediator of the inflammatory response, and increases the production of other inflammatory cytokines such as IL-6 (interleukin-6) (Arvin et al. 1996).

Therefore, the development of a drug that can suppress the production or function of inflammatory cytokines can provide a great possibility to use the drug for the prevention or amelioration of cancer-related pain caused as a side effect of anticancer drug treatment to treat malignancy.

Role of Cytokines in Cognitive Impairment

Chemotherapy-related cognitive impairment (CRCI) is a symptom of decreased memory and concentration. In general, it is called 'chemobrain' or 'chemofog' (Berger et al. 2013). The incidence rate of CRCI in breast cancer patients is reported to be 18-78% (Ahles et al. 2012; Cull et al. 1996). 17-35% of them are known to experience long-term severe CRCI (Ahles et al. 2002; Silberfarb P M. 1983). Chemotherapy is known to induce cognitive impairment in the overall range of attention, executive function, speed of information processing, language and visual memory, and mental motor area (Boykoff et al. 2009; Reid-Arndt et al. 2010). From the end of chemotherapy, language memory, visual memory, and mental processing speed begin to decline, and in some cases, cognitive decline and impairment last for more than five years (de Ruiter et al. 2011; Heflin et al. 2005; Vardy et al. 2008). Cancer patients who are experiencing cognitive decline have difficulty in pre-agreement or decision-making about treatment method (Nelson et al. 2007); in role performance in daily life; in social life because of psychological atrophy; and in adapting to workplace after returning to work, suggesting that CRCI has a negative effect on the adaptation and quality of cancer patient's life (Cheung et al. 2012; Munir et al. 2010; Boykoff et al. 2009; Reid-Arndt et al. 2010).

The exact mechanism of CRCI is not all disclosed but the inflammatory cytokines (TNF-α, IL-6, IL-11, etc.) secreted from those cells damaged by anticancer drug treatment are presumed to be a major cause of CRCI. According to recent studies, inflammatory cytokines act as a major mediator of cognitive decline induced by chemotherapy (Kesler et al. 2013; Ganz et al. 2013; Janelsins et al. 2011). In many clinical studies, the up-regulations of inflammatory cytokines such as TNF-α and IL-6 were observed in cancer patients when they were administered with anticancer agents at the standard dosage. The up-regulations of such cytokines were more significant in those patients who were experiencing cognitive decline, suggesting that the inflammatory cytokine expression pattern is closely related to cognitive function (Tsavaris et al. 2002; Janelsins et al. 2012; Meyers et al. 2005).

Cytokines are known as mediators of neuroendocrine and immune system regulation and can regulate neurotransmitter metabolism, function of neuronal and glial cells, and repair and regeneration of neurons (Ahles et al. 2007; Wilson et al. 2002; Raison et al. 2003). The up-regulated cytokines in the blood of cancer patients treated with chemotherapy pass through the blood-brain barrier and then activate macrophages and microglial cells in the brain, indicating that the production of cytokines increases in the brain tissues to cause inflammatory response. The cytokine-induced inflammatory response stimulates the hypothalamus-pituitary-axis (HPA) responsible for the production of cytokine and the regulation of cortisol secretion in response to physical or mental stress and accordingly induces cognitive decline by increasing oxidative stress in the brain tissues (Wang et al. 2015).

Therefore, the development of a drug that can suppress the production or function of inflammatory cytokines can provide a great possibility to use the drug for the prevention or amelioration of cognitive decline caused as a side effect of the anticancer drug treatment to treat malignancy because such a drug can protect the brain from inflammation and damage.

Role of Cytokines in Maintaining Hematopoetic Stem Cells

Hematopoietic stem cells are auto-replicable. They can be differentiated into various bone marrow and lymphocyte progenitor cells and can be functioning to maintain hematopoietic system in vivo (Summers et al. 2004). The Bone marrow has a specific microenvironment (niche) which helps hematopoietic stem cells to be self-replicated and differentiated into various cells. In such a microenvironment, the self-replication, interphase, and differentiation of hematopoietic stem cells are controlled, and the fate or size of hematopoietic stem cells is determined (Schofield et al. 1978).

Bone marrow damage is one of the most frequently observed side effects in the course of cancer treatment using anticancer agents, which limits the dosage of anticancer agents, resulting in inefficiency of cancer treatment. Chemotherapy using an anticancer agent destroys not only cancer cells but also normal cells, especially hematopoietic stem cells, causing a serious problem of the malfunction of hematopoietic function and immune function in the body. Anticancer agents generally used for the treatment of cancer induce apoptosis of hematopoietic cells and hematopoietic stem cells, differentiation and aging of hematopoietic stem cells and damage to bone marrow stroma and hematopoietic stem cell niche, resulting in acute or chronic bone marrow damage (Shao et al. 2010; Lotem et al. 1993; Wlodarski et al. 1998; Yu et al. 2010; Testa et al. 1985). Hematopoietic stem cells are in the interphase in the microenvironment of the bone marrow and if necessary they enter the differentiation stage. Those hematopoietic stem cells in the interphase are not easily damaged by anticancer treatment (Corazza et al. 2004). However, in the inflammation condition caused by anticancer agents, the differentiation of hematopoietic stem cells is accelerated and such activated cells are targeted by the anticancer agents so that the hematopoietic stem cells in the bone marrow are eventually depleted (King et al. 2011). Normal hematopoietic stem cells are known to play an important role in maintaining immune homeostasis by reducing inflammatory cytokines such as TNF-α, IL-1β, and IFN-gamma and by increasing anti-inflammatory cytokines such as IL-10 (Siniscalco et al. 2013). However, the over-production of TNF, known as an inflammatory cytokine, interrupts the dormancy of hematopoietic stem cells (Bryder et al. 2001; Dybedal et al. 2001), indicating that the maintenance of the number and function of hematopoietic stem cells is important for preventing or improving the side effects caused by anticancer agents.

Therefore, the development of a drug that can maintain and improve the number and function of hematopoietic stem cells by maintaining the resting state of hematopoietic stem cells through the control of inflammatory cytokines provides a great possibility to use the drug for the prevention or amelioration of various side effects related to anticancer drug treatment.

Naphthoquinone-based compounds are known as active ingredients for some pharmaceutical compositions. Among them, dunnione is divided into two structures, alpha-dunnione (2,3-dihydro-2,3,3-trimethyl naphtho [1,2-b]furan-4,9-dione) and dunnione (2,3-dihydro-2,3,3-trimethyl naphtho [1,2-b]furan-4,5-dione), which can be obtained from the leaves of *Streptocarpus dunnii* or from several species of Calceolaria distributed in South America. In the meantime, β-lapachone (3,4-Dihydro-2,2-dimethyl-2H-naphtho (1,2-b) pyran-5,6-dione) is obtained from laphacho tree (*Tabebuia avellanedae*) distributed in South America.

Referring to the patent papers applied or registered so far which describe the pharmacokinetics, β-lapachone or its derivatives can be used for the prevention of leukopenia, mononucleosis, and lymphocytopenia observed in the course of radiotherapy for cancer treatment (U.S. Pat. No. 7,649,013 B2). It has been also reported that beta-lapachone generates reactive oxygen species such as H2O2 by NQO-1 (NAD (P) H quinone oxidoreductase-1) dependent futile redox cycling, and this reactive oxygen species causes DNA damage such as single strand break in cancer cell DNA which leads to over-activation of PARP-1 (Poly-ADP ribose polymerase-1), by which NAD+ and ATP are depleted eventually and cancer cells are going to die (Pink et al. 2000; Bey et al. 2013). Queiroz M L, et al disclosed that β-lapachone and *Tabebuia avellanedae* extract were effective in ameliorating bone marrow suppression which was caused in Ehrlich ascites tumor-bearing mice without anticancer chemotherapy (Queiroz et al. 2008). KT & G Life Science reported that β-lapachone and dunnione were efficient in preventing and treating obesity, diabetes, metabolic syndrome, neurodegenerative diseases, and mitochondrial dysfunction related diseases (U.S. Pat. No. 9,066,922, B2). Lee J S et al reported that β-lapachone was able to improve aging health and cognitive ability by regulating NAD metabolism (Lee et al. 2012). Jose Angel et al disclosed that the extract of *Tabebuia avellanedae* originated from β-lapachone extract was efficient in improving the symptoms of Parkinson's disease (U.S. Pat. No. 7,553,503 B2).

The present inventors and Park D et al had reported that β-lapachone and dunnione were efficient in improving the recovery of damages in the kidney and various other organs caused as side effects of anticancer drug treatment (Oh et al. 2014; Kim et al. 2014; Park et al. 2015). In particular, in the previous study of the present inventors, it was confirmed that β-lapachone increased intracellular NAD+NQO-1 dose-dependently and thereby β-lapachone showed the effect of inhibiting cancer-related DNA damage and the hyperactivation of PARP-1 and of protecting kidney and inner ear from being damaged as a result. Tzeng et al also reported that 3-lapachone was able to prevent lung injury in the lung injury animal model caused by endotoxin treatment (Tzeng et al. 2003). Duke University also reported that naphthoquinone-based compounds such as β-lapachone were efficient in treating and improving lung diseases and bronchial diseases (US20140155361). In addition, Kwak T H et al reported that naphthoquinone-based compounds such as β-lapachone were efficient in improving and treating heart disease (US 2014/0154319 A1).

However, there are no reports made yet about the effect or role of naphthoquinone-based compounds such as β-lapachone in preventing or ameliorating fatigue, cachexia, pain, cognitive decline, and hematopoietic stem cell reduction caused in the course of anticancer drug treatment.

Therefore, the present inventors have studied to screen a material efficient in preventing or improving cancer-related fatigue, cachexia, pain, cognitive decline, and hematopoietic stem cell reduction. As a result, the present inventors confirmed that dunnione and β-lapachone, the naphthoquinone-based compounds, had the activity to reduce the secretion and production of inflammatory cytokines increased by anticancer drug treatment, to alleviate fatigue, to ameliorate cachexia, to reduce pain, to improve cognitive ability, and to prevent hematopoietic stem cell reduction. Thereafter, the present inventors confirmed that the naphthoquinone-based compounds, pharmaceutically acceptable salts, prodrugs, solvates or isomers thereof could be effectively used as a pharmaceutical composition for preventing or ameliorating any one or more side effects related to anticancer drug treatment selected from the group consisting of fatigue, cachexia, pain, cognitive decline, and hematopoietic stem cell reduction, leading to the completion of the present invention.

PRIOR ART REFERENCE

Patent Reference

ARQULE, INC. et al, Methods of protecting against radiation injury. U.S. Pat. No. 7,649,013 B2
Duke University Durham N.C., Method for treating lung disease. US 20140155361
Jose Angel, Olalde Rangel, Phyto-neutriceutical synergistic composition for Parkinson's disease. U.S. Pat. No. 7,553,503 B2
MD BIOALPHA CO., LTD./KT&G CO., LTD, Pharmaceutical composition for the treatment or prevention of diseases involving obesity, diabetes, metabolic syndrome, neuro-degenerative diseases and mitochondria dysfunction diseases. U.S. Pat. No. 9,066,922, B2
Taehwan KWAK/Myung-Gyu Park, Pharmaceutical composition for the treatment or prevention of cardiac disease. US 2014/0154319 A1

Non-Patent Reference

Ahles T A et al. Neuropsychologic impact of standard-dose systemic chemotherapy in long-term survivors of breast cancer and lymphoma. J Clin Oncol 2002; 20 (2): 485-493
Ahles T A, Root J C, Ryan E L. Cancer- and cancer treatment-associated cognitive change: an update on the state of the science. J Clin Oncol 2012; 30 (30): 3675-3676
Ahles T A, Saykin A J. Candidate mechanisms for chemotherapy-induced cognitive changes. Nat Rev Cancer 2007; 7 (3): 192-201
Aoyagi T, Terracina K P, Raza A, Matsubara H, Takabe K. Cancer cachexia, mechanism and treatment. World J Gastrointest Oncol. 2015; 7 (4): 17-29
Argiles J M, Busquets S, Lopez-Soriano F J. The pivotal role of cytokines in muscle wasting during cancer. Int J Biochem Cell Biol. 2005; 37 (10): 2036-2046
Arvin B, Neville L F, Barone F C, Feuerstein G Z. The role of inflammation and cytokines in brain injury. Neurosci Biobehav Rev. 1996; 20:445-452
Babar T, Blomberg C, Yan X. Anti-HER2 cancer therapy and cardiotoxicity. Current Pharmaceutical Design 2014; 20:4911-4919 Barsevick A, Frost M, Zwinderman A, Hall P, Halyard M.
GENEQOL Consortium. I'm so tired: biological and genetic mechanisms of cancer-related fatigue. Qual Life Res. 2010; 19 (10): 1419-1427
Bendall L J & Bradstock K F. G-CSF: From granulopoietic stimulant to bone marrow stem cell mobilizing agent. Cytokine Growth Factor Rev. 2014; 25:355-67.
Berger A, Shuster J L, Von Roenn J H. Principles and practice of palliative care and supportive oncology. vol. xvii. 4th ed. Philadelphia: Wolters Kluwer Health/Lippincott Williams & Wilkins; 2013
Bethea J R, Gillespie G Y, Chung I Y, Benveniste E N. Tumor necrosis factor production and receptor expression by a human malignant glioma cell line, D54-M G. J Neuroimmunol. 1990; 30:1-13
Bey E. A. et al. Catalase abrogates beta-lapachone-induced PARP1 hyperactivation-directed programmed necrosis in NQO1-positive breast cancers. Molecular cancer therapeutics 2013; 12, 2110-2120.
Blesch, et al. Correlates of fatigue in people with breast or lung cancer. Oncol Nurs Forum 1991; 18 (1): 81-87
Boykoff N, Moieni M, Subramanian S K. Confronting chemobrain: an in-depth look at survivors' reports of impact on work, social networks, and health care response. J Cancer Surviv. 2009; 3:1-10
Braun T P, Szumowski M, Levasseur P R, Grossberg A J, Zhu X, Agarwal A, Marks D L. Muscle atrophy in response to cytotoxic chemotherapy is dependent on intact glucocorticoid signaling in skeletal muscle. PLOS One. 2014; 9 (9): e106489
Brown R C, Davis T P. Calcium Modulation of Adherens and Tight Junction Function: A Potential Mechanism for Blood-Brain Barrier Disruption After Stroke. Stroke. 2002; 33:1706-1711
Bruera E. Anorexia, cachexia and nutrition. BMJ 1997; 315:1219-22.

Bryder D, Ramsfjell V, Dybedal I, Theilgaard-Monch K, Hogerkorp C M, Adolfsson J, Borge O J, Jacobsen S E. Self-renewal of multipotent long-term repopulating hematopoietic stem cells is negatively regulated by FAS and tumor necrosis factor receptor activation. J Exp Med. 2001; 194:941-952

Cetean S, Cainap C, Constantin A M, Cainap S, Gherman A, Oprean L, Hangan A, Oprean R. The importance of the granulocyte-colony stimulating factor in oncology. Clujul Med. 2015; 88:468-72.

Cheung Y T, Lim S R, Ho H K, Chan A. Cytokines as mediators of chemotherapy-associated cognitive changes: current evidence, limitations and directions for future research. PLOS One. 2013; 8 (12): e81234 Cheung Y T, Maung Shwe H G, Tan Y P, Fan G K T, Ng R C H, et al. Cognitive changes in multiethnic Asian breast cancer patients: A focus group study. Ann Oncol 2012; 23:2547-2552

Cheung Y T, Ng T, Shwe M, Ho H K, Foo K M, Cham M T, Lee J A, Fan G, Tan Y P, Yong W S, Madhukumar P, Loo S K, Ang S F, Wong M, Chay W Y, Ooi W S, Dent R A, Yap Y S, Ng R, Chan A. Association of proinflammatory cytokines and chemotherapy-associated cognitive impairment in breast cancer patients: a multi-centered, prospective, cohort study. Ann Oncol. 2015; 26 (7): 1446-1451

Choi J I, Svensson C I, Koehrn F J, Bhuskute A, Sorkin L S. Peripheral inflammation induces tumor necrosis factor dependent AMPA receptor trafficking and Akt phosphorylation in spinal cord in addition to pain behavior. Pain 2010; 149 (2): 243-253

Cleeland C S, Bennett G J, Dantzer R, Dougherty P M, Dunn A J, Meyers C A, Miller A H, Payne R, Reuben J M, Wang X S et al. Are the symptoms of cancer and cancer treatment due to a shared biologic mechanism? A cytokine-immunologic model of cancer symptoms. Cancer 2003; 97:2919-2925

Cleeland C S. The impact of pain on the patient with cancer. Cancer. 1984; 54 (11 Suppl): 2635-2641

Conti P, Kempuraj D. Important role of mast cells in multiple sclerosis. Mult Scler Relat Disord. 2016; 5:77-80

Corazza F, Hermans C, Ferster A, Fondu P, Demulder A, Sariban E. Bone marrow stroma damage induced by chemotherapy for acute lymphoblastic leukemia in children. Pediatr Res 2004; 55:152-158

Cull A, Hay C, Love S B, Mackie M, Smets E, Stewart M. What do cancer patients mean when they complain of concentration and memory problems? Br J Cancer 1996; 74 (10): 1674-1679

Curt G A, Breitbart W, Cella D, Groopman J E, Horning S J, Itri L M et al. Impact of cancer-related fatigue on the lives of patients: new findings from the fatigue coalition. Oncologists 2000; 5:353-360

Dash C, Randolph-Jackson P D, Isaacs C, Mills M, Makambi K, Watkins V V, Adams-Campbell L L. An exercise trial to reduce cancer related fatigue in African American breast cancer patients undergoing radiation therapy: Design, rationale, and methods. Contemp Clin Trials. 2016; 47:153-157 de Ruiter M B et al. Cerebral hyporesponsiveness and cognitive impairment 10 years after chemotherapy for breast cancer. Hum Brain Mapp 2011; 32 (8): 1206-1209

Delaney A, Fleetwood-Walker S M, Colvin L A and Fallon M. Translational medicine: cancer pain mechanisms and management. British Journal of Anaesthesia 2008; 101 (1): 87-94

Dybedal I, Bryder D, Fossum A, Rusten L S, Jacobsen S E. Tumor necrosis factor (TNF)-mediated activation of the p55 TNF receptor negatively regulates maintenance of cycling reconstituting human hematopoietic stem cells. Blood. 2001; 98:1782-1791

Edgar D M, Seidel W F. Modafinil induces wakefulness without intensifying motor activity or subsequent rebound hypersomnolence in the rat. J Pharmacol Exp Ther. 1997; 283 (2): 757-769

Engineer D R, Garcia J M. Leptin in anorexia and cachexia syndrome. Int J Pept. 2012; 2012:287457

Ezeoke C C, Morley J E. Pathophysiology of anorexia in the cancer cachexia syndrome. J Cachexia Sarcopenia Muscle. 2015; 6 (4): 287-302

Fang H, Jiang W, Cheng J, Lu Y, Liu A, Kan L, Dahmen U. Balancing Innate Immunity and Inflammatory State via Modulation of Neutrophil Function: A Novel Strategy to Fight Sepsis. J Immunol Res. 2015; 2015:187048

Farquhar-Smith P. Chemotherapy-induced neuropathic pain. Curr. Opin. Support Palliat. Care. 2011; 5 (1): 1-7

Ganz P A, Bower J E, Kwan L, Castellon S A, Silverman D H S, et al. Does tumor necrosis factor-alpha (TNF-α) play a role in post-chemotherapy cerebral dysfunction? Brain Behav Immun 2013; 30 Suppl: S99-108

Gaultier A, Arandjelovic S, Li X, Janes J, Dragojlovic N, Zhou G P, Dolkas J, Myers R R, Gonias S L, Campana W M. A shed form of LDL receptor-related protein-1 regulates peripheral nerve injury and neuropathic pain in rodents. J Clin Invest. 2008; 118 (1): 161-172

Gearing A J, Beckett P, Christodoulou M, Churchill M, Clements J, Davidson A H, Drummond A H, Galloway W A, Gilbert R, Gordon J L. Processing of tumor necrosis factor-alpha precursor by metalloprot-einases. Nature. 1994; 370:555-557

Glaus A. Fatigue in patients with cancer. Analysis and assessment. Recent Results in Cancer Research, 1998; 145 (1-1): 1-172

Haghighat S, Akbari M E, Holakouei K, Rahimi A, Montazeri A. Factors predicting fatigue in breast cancer patients. Support Care Cancer. 2003; 11 (8): 533-538

Heflin L H et al. Cancer as a risk factor for long-term cognitive deficits and dementia. J Natl Cancer Inst 2005; 97 (11): 854-856

Hermant J F, Rambert F A, Duteil J. Awakening properties of modafinil: effect on nocturnal activity in monkeys (*Macaca mulatta*) after acute and repeated administration. Psychopharmacology (Berl). 1991; 103 (1): 28-32

Hofman M, Ryan J L, Figueroa-Moseley C D, Jean-Pierre P, Morrow G R. Cancer-related fatigue: the scale of the problem. Oncologist. 2007; 12 Suppl 1:4-10

Hovey E, de Souza P, Marx G, Parente P, Rapke T, Hill A, Bonaventura A, Michele A, Craft P, Abdi E, Lloyd A. MOTIF investigators. Phase III, randomized, double-blind, placebo-controlled study of modafinil for fatigue in patients treated with docetaxel-based chemotherapy. Support Care Cancer. 2014; 22 (5): 1233-1242

Huber J D, Witt K A, Horn S, Egleton R D, Mark K S, Davis T P. Inflammatory pain alters blood-brain barrier permeability and tight junctional protein expression. Am J Physiol. 2001; 280: H1241-1248

Hwang S S, Chang V T, Rue M, Kasimis B. Multidimensional independent predictors of cancer-related fatigue. J Pain Symptom Manage. 2003; 26 (1): 604-614

Inacio Pinto N, Carnier J, Oyama L M, Otoch J P, Alcantara P S, Tokeshi F, Nascimento C M. Cancer as a Proinflammatory Environment: Metastasis and Cachexia. Mediators Inflamm. 2015; 2015:791060

Janelsins M C, Mustian K M, Palesh O G, Mohile S G, Peppone L J, et al. Differential expression of cytokines in breast cancer patients receiving different chemotherapies: implications for cognitive impairment research. Support Care Cancer 2011; 20:831-839

Janes K, Little J W, Li C, Bryant L, Chen C, Chen Z, Kamocki K, Doyle T, Snider A, Esposito E, Cuzzocrea S, Bieberich E, Obeid L, Petrache I, Nicol G, Neumann W L, Salvemini D. The development and maintenance of paclitaxel-induced neuropathic pain require activation of the sphingosine 1-phosphate receptor subtype 1. J Biol Chem. 2014; 289 (30): 21082-21097

Keep R F, Xiang J, Ennis S R, Andjelkovic A, Hua Y, Xi G, Hoff J T. Blood-brain barrier function in intracerebral hemorrhage. Acta Neurochir Suppl. 2008; 105:73-77

Kern K A, Norton J A. Cancer Cathexia. JPEN J Parenteral and Enteral Nutr. 1988; 12 (3): 286-298

Kesler S, Janelsins M, Koovakkattu D, Palesh O, Mustian K, et al. Reduced hippocampal volume and verbal memory performance associated with interleukin-6 and tumor necrosis factor-alpha levels in chemotherapy treated breast cancer survivors. Brain Behav Immun 2013; 30 Suppl: S109-116

Kim H J, Oh G S, Shen A, Lee S B, Choe S K, Kwon K B, Lee S, Seo K S, Kwak T H, Park R, So H S. Augmentation of NAD (+) by NQO1 attenuates cisplatin-mediated hearing impairment. Cell Death Dis. 2014 Jun. 12; 5: e1292.

Kim H K, Nunes P V, Oliveira K C, Young L T, Lafer B. Neuropathological relationship between major depression and dementia: A hypothetical model and review. Prog Neuropsychopharmacol Biol Psychiatry. 2016; 67:51-57

King K Y, Goodell M A. Inflammatory modulation of HSCs: viewing the HSC as a foundation for the immune response. Nat Rev Immunol. 2011; 11:685-692

Lahdevirta J, Maury C P, Teppo A M, Repo H. Am J Med. Elevated levels of circulating cachectin/tumor necrosis factor in patients with acquired immunodeficiency syndrome. 1988; 85 (3): 289-291

Laird B J, McMillan D C, Fayers P, Fearon K, Kaasa S, Fallon M T, Klepstad P. The systemic inflammatory response and its relationship to pain and other symptoms in advanced cancer. Oncologist. 2013; 18 (9): 1050-5.

Laird B J, Scott A C, Colvin L A et al. Cancer pain and its relationship to systemic inflammation: An exploratory study. Pain 2011; 152:460-463

Lee J S, Park A H, Lee S H, Lee S H, Kim J H, Yang S J, Yeom Y I, Kwak T H, Lee D, Lee S J, Lee C H, Kim J M, Kim D. Beta-lapachone, a modulator of NAD metabolism.

Leitner G C, Vogelsang H. Pharmacological- and non-pharmacological therapeutic approaches in inflammatory bowel disease in adults. World J Gastrointest Pharmacol Ther. 2016; 7 (1): 5-20

Lelbach A, Muzes G, Feher J. Current perspectives of catabolic mediators of cancer cachexia. Med Sci Monit. 2007; 13 (9): RA168-173

Liu S and Kurzrock R. Toxicity of targeted therapy: Implications for response and impact of genetic polymorphisms. Cancer Treatment Review 2014; 49 (7): 883-891

Lopez Gonzalez I, Garcia-Esparcia P, Llorens F, Ferrer I. Genetic and Transcriptomic Profiles of Inflammation in Neurodegenerative Diseases: Alzheimer, Parkinson, Creutzfeldt-Jakob and Tauopathies. Int J Mol Sci. 2016; 17 (2). pii: E206

Lotem J, Sachs L. Hematopoietic cells from mice deficient in wild-type p53 are more resistant to induction of apoptosis by some agents. Blood. 1993; 82:1092-1096

Madeddu C, Mantovani G, Gramignano G, Maccio A. Advances in pharmacologic strategies for cancer cachexia. Expert Opin Pharmacother. 2015; 16 (14): 2163-2177

Manir K S, Bhadra K, Kumar G, Manna A, Patra N B, Sarkar S K. Fatigue in breast cancer patients on adjuvant treatment: course and prevalence. Indian J Palliat Care. 2012; 18 (2): 109-116

Mantyh P W, Clohisy D R, Koltzenburg M, and Hunt S P. Molecular mechanisms of cancer pain, Nature Reviews Cancer 2002; 2 (3): 201-209

Mantyh P W, Clohisy D R, Koltzenburg M, Hunt S P. Molecular mechanisms of cancer pain. Nat Rev Cancer. 2002; 2 (3): 201-209

Mark D. DeBoer. Ghrelin and cachexia: Will treatment with GHSR-1a agonists make a difference for patients suffering from chronic wasting syndromes? Mol Cell Endocrinol. 2011; 340 (1): 97-105

McCabe A & MacNamara K C. Macrophages: Key regulators of steady-state and demand-adapted hematopoiesis. Exp Hematol. 2016; 44:213-22.

McGuire D B. Advances in control of cancer pain. Nurs Clin North Am. 1987; 22 (3): 677-690

Meriggi F. Cancer-related fatigue: still an enigma to be solved quickly. Rev Recent Clin Trials. 2014; 9 (4): 267-270

Meyers C A, Albitar M, Estey E. Cognitive impairment, fatigue, and cytokine levels in patients with acute myelogenous leukemia or myelodysplastic syndrome. Cancer 2005; 104 (4): 788-793

Miaskowski C, Lee K A. Pain, fatigue, and sleep disturbances in oncology outpatients receiving radiation therapy for bone metastasis: a pilot study. J Pain Symptom Manage. 1999; 17 (5): 320-332

Munir F, Burrows J, Yarker J, Kalawsky K, Bains M. Women' perceptions of chemotherapy-induced cognitive side affect on work ability: A focus group study. J Clin Nurs 2010; 19:1362-1370

National Cancer Information Center. Cancer Information Service. 2015. Available at: http://www.cancer.go.kr National Cancer Institute. Targeted Cancer Therapies. 2016. Available at: http://www.cancer.gov National Comprehensive Cancer Network. Clinical Practice Guidelines in Oncology. Cancer Related Fatigue version 1. 2016. Available at: http://www.nccn.org/professionals/physician_gls/pdf/fatigue.pdf Neefjes E C, van der Vorst M J, Blauwhoff-Buskermolen S, Verheul H M. Aiming for a better understanding and management of cancer-related fatigue. Oncologist. 2013; 18 (10): 1135-1143

Nelson C J, Nandy N, Roth A J, Chemotherapy and cognitive deficits: mechanisms, findings, and potential interventions. Palliat Support Care. 2007; 5 (3): 273-280

Nelson K A, Walsh D, Sheehan F A. The cancer anorexia-cachexia syndrome. J Clin Oncol. 1994; 12 (1): 213-225

Oh G S, Kim H J, Choi J H, Shen A, Choe S K, *Karna* A, Lee S H, Jo H J, Yang S H, Kwak T H, Lee C H, Park R, So H S. Pharmacological activation of NQO1 increases NAD levels and attenuates cisplatin-mediated acute kidney injury in mice. Kidney Int. 2014; 85 (3): 547-560.

Panckeri K A, Schotland H M, Pack A I, Hendricks J C. Modafinil decreases hypersomnolence in the English bulldog, a natural animal model of sleep-disordered breathing. Sleep. 1996; 19 (8): 626-631

Park D, Jo I G, Jang J Y, Kwak T H, Yoo S K, Jeon J H, Choi E K, Joo S S, Kim O, Kim Y B. A Dunnione Compound MB12662 Improves Cisplatin-Induced Tissue Injury and Emesis. Biomol Ther (Seoul). 2015; 23 (5): 449-457

Pietras E M, Reynaud D, Kang Y A, Carlin D, Calero-Nieto F J, Leavitt A D, Stuart J M, Gottgens B, Passegue E. Functionally Distinct Subsets of Lineage-Biased Multipotent Progenitors Control Blood Production in Normal and Regenerative Conditions. Cell Stem Cell. 2015; 17:35-46.

Pink J. J. et al. NAD (P) H: Quinone oxidoreductase activity is the principal determinant of beta-lapachone cytotoxicity. The Journal of biological chemistry 2000; 275, 5416-5424.

Polomano R C, Mannes A J, Clark U S, Bennett G J. A painful peripheral neuropathy in the rat produced by the chemotherapeutic drug, paclitaxel. Pain 2001; 94 (3): 293-304 prevents health declines in aged mice. PLOS One. 2012; 7 (10): e47122.

Queiroz M L et al. Comparative studies of the effects of *Tabebuia avellanedae* bark extract and beta-lapachone on the hematopoietic response of tumor-bearing mice. J. Ethnopharmacol. 2008; 117 (2): 228-235

Raison C L, Miller A H. Depression in cancer: new developments regarding diagnosis and treatment. Biol Psychiatry 2003; 54 (3): 283-294

Reid-Arndt S A, Hsieh C, Perry M C Neuropsychological functioning and quality of life during the first year after completing chemotherapy for breast cancer. Psychooncology 2010; 19:535-544.

Ridker P M. From C-Reactive Protein to Interleukin-6 to Interleukin-1: Moving Upstream To Identify Novel Targets for Atheroprotection. Circ Res. 2016; 118 (1): 145-156

Ryan J L, Carroll J K, Ryan E P, Mustian K M, Fiscella K, Morrow G R. Mechanisms of cancer-related fatigue. Oncologist. 2007; 12 Suppl 1:22-34

Schofield R. The relationship between the spleen colony-forming cell and the haematopoietic stem cell. Blood Cells 1978; 4:7-25

Schulte R, Wilson N K, Prick J C, Cossetti C, Maj M K, Gottgens B, Kent D G. Index sorting resolves heterogeneous murine hematopoietic stem cell populations. Exp Hematol. 2015; 43:803-811.

Shao L, Sun Y, Zhang Z, et al. Deletion of proapoptotic Puma selectively protects hematopoietic stem and progenitor cells against high-dose radiation. Blood. 2010; 115:4707-4714

Shelton J, Nishino S, Vaught J, Dement W C, Mignot E. Comparative effects of modafinil and amphetamine on daytime sleepiness and cataplexy of narcoleptic dogs. Sleep. 1995; 18 (10): 817-826

Silberfarb P M. Chemotherapy and cognitive defects in cancer patients. Annu Rev Med 1983; 34:35-36

Siniscalco D, Bradstreet J J, Antonucci N. Therapeutic role of hematopoietic stem cells in autism spectrum disorder-related inflammation. Front Immunol. 2013; 4:140

Slaviero K A, Read J A, Clarke S J, Rivory L P. Baseline nutritional assessment in advanced cancer patients receiving palliative chemotherapy. Nutr Cancer 2003; 46:148-157

Sommer C, Kress M. Recent findings on how proinflammatory cytokines cause pain: peripheral mechanisms in inflammatory and neuropathic hyperalgesia. Neurosci Lett. 2004; 361 (1-3): 184-187

Stark T, Livas L, Kyprianou N. Inflammation in prostate cancer progression and therapeutic targeting. Transl Androl Urol. 2015; 4 (4): 455-463

Stark T, Livas L, Kyprianou N. Inflammation in prostate cancer progression and therapeutic targeting. Transl Androl Urol. 2015; 4 (4): 455-463

Summers Y J, Heyworth C M, de Wynter E A, Hart C A, Chang J, Testa N G. AC133+GO cells from cord blood show a high incidence of long-term culture-initiating cells and a capacity for more than 100 million-fold amplification of colony-forming cells in vitro. Stem Cells 2004; 22:704-715

Testa N G, Hendry J H, Molineux G. Long-term bone marrow damage in experimental systems and in patients after radiation or chemotherapy. Anticancer Res. 1985; 5:101-110

Teunissen S C, Wesker W, Kruitwagen C et al. Symptom prevalence in patients with incurable cancer: A systematic review. J Pain Symptom Manage 2007; 34:94-104

Tian L, Lu H J, Lin L, Hu Y. Effects of aerobic exercise on cancer-related fatigue: a meta-analysis of randomized controlled trials. Support Care Cancer. 2015

Touret M, Sallanon-Moulin M, Jouvet M. Awakening properties of modafinil without paradoxical sleep rebound: comparative study with amphetamine in the rat. Neurosci Lett. 1995; 189 (1): 43-46

Tsai J S, Wu C H, Chiu T Y, Hu W Y, Chen C Y. Symptom patterns of advanced cancer patients in a palliative care unit. Palliat Med. 2006; 20 (6): 617-622

Tsavaris N et al. Immune changes in patients with advanced breast cancer undergoing chemotherapy with taxanes. Br J Cancer 2002; 87 (1): 21-27

Tzeng H P, Ho F M, Chao K F, Kuo M L, Lin-Shiau S Y, Liu S H. beta-Lapachone reduces endotoxin-induced macrophage activation and lung edema and mortality. Am J Respir Crit Care Med. 2003; 168 (1): 85-91

Van Cutsem E, Arends J. The causes and consequences of cancer-associated malnutrition. Eur J Oncol Nurs. 2005; 9 Suppl 2: S51-63

Vardy J et al. Cancer and cancer-therapy related cognitive dysfunction: an international perspective from the Venice cognitive workshop. Ann Oncol 2008; 19 (4): 623-629

Vendrell I, Macedo D, Alho I, Dionisio M R, Costa L. Treatment of Cancer Pain by Targeting Cytokines. Mediators Inflamm. 2015; 2015:984570

Walsmith J, Roubenoff R. Cachexia in rheumatoid arthritis. Int J Cardiol. 2002; 85 (1): 89-99

Wang X M, Lehky T J, Brell J M, Dorsey S G. Discovering cytokines as targets for chemotherapy-induced painful peripheral neuropathy. Cytokine 2012; 59:3-9

Wang X M, Walitt B, Saligan L, Tiwari A F, Cheung C W, Zhang Z J. Chemobrain: A critical review and causal hypothesis of link between cytokines and epigenetic reprogramming associated with chemotherapy. Cytokine 2015; 72:86-96.

Weis J. Cancer-related fatigue: prevalence, assessment, and treatment strategies. Expert. Rev. Pharmacoecon Outcomes Res. 2011; 11 (4): 441-446

Weymann K B, Wood L J, Zhu X, Marks D L. A role for orexin in cytotoxic chemotherapy-induced fatigue. Brain Behav Immun. 2014; 37:84-94

Wilson C J, Finch C E, Cohen H J. Cytokines and cognition—he case for a head-to-toe inflammatory paradigm. J Am Geriatr Soc 2002; 50 (12): 2041-2056

Winningham M L, Nail L M, Burke M B, Brophy L, Cimprich B, Jones L S et al. Fatigue and the cancer experience: The state of the knowledge. Oncology Nursing Forum. 1994; 21:23-36

Wlodarski P, Wasik M, Ratajczak M Z, et al. Role of p53 in hematopoietic recovery after cytotoxic treatment. Blood. 1998; 91:2998-3006

Wognum A. W. Hematopoietic Stem and Progenitor Cells. Mini-Review Stemcell Technologies. 2015.

Wood L J, Nail L M, Gilster A, Winters K A, Elsea C R. Cancer chemotherapy-related symptoms: to suggest a role for proinflammatory cytokines. Oncol Nurs Forum. 2006; 33 (3): 535-542

Wyke S M, Russell S T, and Tisdale M J. Induction of proteasome expression in skeletal muscle is attenuated by inhibitors of NF-κB activation. Br J Cancer. 2004; 91 (9): 1742-1750

Xiao W H, Zheng H, Bennett G J. Characterization of oxaliplatin-induced chronic painful peripheral neuropathy in the rat and comparison with the neuropathy induced by paclitaxel. Neuroscience 2012; 203:194-206

Yu H, Shen H, Yuan Y, et al. Deletion of puma protects hematopoietic stem cells and confers long-term survival in response to high-dose gamma-irradiation. Blood. 2010; 115:3472-3480

Zhang J M, An J. Cytokines, inflammation, and pain. Int Anesthesiol Clin. 2007; 45 (2): 27-37

Zhao J, Brault J J, Schild A, Cao P, Sandri M, Schiaffino S, et al. FoxO3 coordinately activates protein degradation by the autophagic/lysosomal and proteasomal pathways in atrophying muscle cells. Cell Metab. 2007; 6:472-483

SUMMARY OF THE INVENTION

It is an object of the present invention to provide a pharmaceutical composition comprising a naphthoquinone-based compound, a pharmaceutically acceptable salt thereof, a prodrug thereof, a solvate thereof or an isomer thereof as an active ingredient for preventing or ameliorating any one or more side effects related to anticancer drug treatment selected from the group consisting of fatigue, cachexia, pain, cognitive decline, and hematopoietic stem cell reduction.

To achieve the above object, the present invention provides a pharmaceutical composition comprising the compound represented by formula 1 or formula 2 below, a pharmaceutically acceptable salt thereof, a prodrug thereof, a solvate thereof or an isomer thereof as an active ingredient for preventing or ameliorating any one or more side effects related to anticancer drug treatment selected from the group consisting of fatigue, cachexia, pain, cognitive decline, and hematopoietic stem cell reduction:

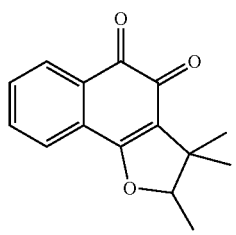

[Formula 1]

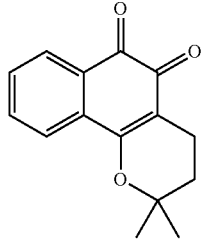

[Formula 2]

The present invention also provides a method for preventing or ameliorating any one or more side effects related to anticancer drug treatment selected from the group consisting of fatigue, cachexia, pain, cognitive decline, and hematopoietic stem cell reduction, which comprises the step of administering the compound represented by formula 1 or formula 2, a pharmaceutically acceptable salt thereof, a prodrug thereof, a solvate thereof or an isomer thereof to mammals.

In addition, the present invention provides a use of the compound represented by formula 1 or formula 2, a pharmaceutically acceptable salt thereof, a prodrug thereof, a solvate thereof or an isomer thereof for the preparation of a drug for preventing or ameliorating any one or more side effects related to anticancer drug treatment selected from the group consisting of fatigue, cachexia, pain, cognitive decline, and hematopoietic stem cell reduction.

Advantageous Effect

In this invention, the naphthoquinone-based compounds such as dunnione and β-lapachone are confirmed to reduce the secretion and production of inflammatory cytokines which are increased by the anticancer drug treatment, and prevent fatigue, cachexia, cognitive decline, and hematopoietic stem cell reduction which are side effects associated with anticancer drug treatment. Therefore, the naphthoquinone-based compounds, pharmaceutically acceptable salts, prodrugs, solvates or isomers thereof can be effectively used as a pharmaceutical composition for preventing or ameliorating any one or more side effects related to anticancer drug treatment selected from the group consisting of fatigue, cachexia, pain, cognitive decline, and hematopoietic stem cell reduction.

BRIEF DESCRIPTION OF THE DRAWINGS

The patent file contains at least one drawing executed in color. Copies of this patent with color drawing(s) will be provided by the Patent and Trademark Office upon request and payment of the necessary fee.

The application of the preferred embodiments of the present invention is best understood with reference to the accompanying drawings, wherein.

Control: PBS treated group; ADR: adriamycin (4 mg/kg× 3) treated group; ADR+Dun: adriamycin and dunnione (20 mg/kg) co-treated group; Dun: dunnione (20 mg/kg) treated group.

*p<0.05: comparison of control group and adriamycin treated group;

p<0.05: comparison of adriamycin treated group and dunnione treated group.

Figure 2:
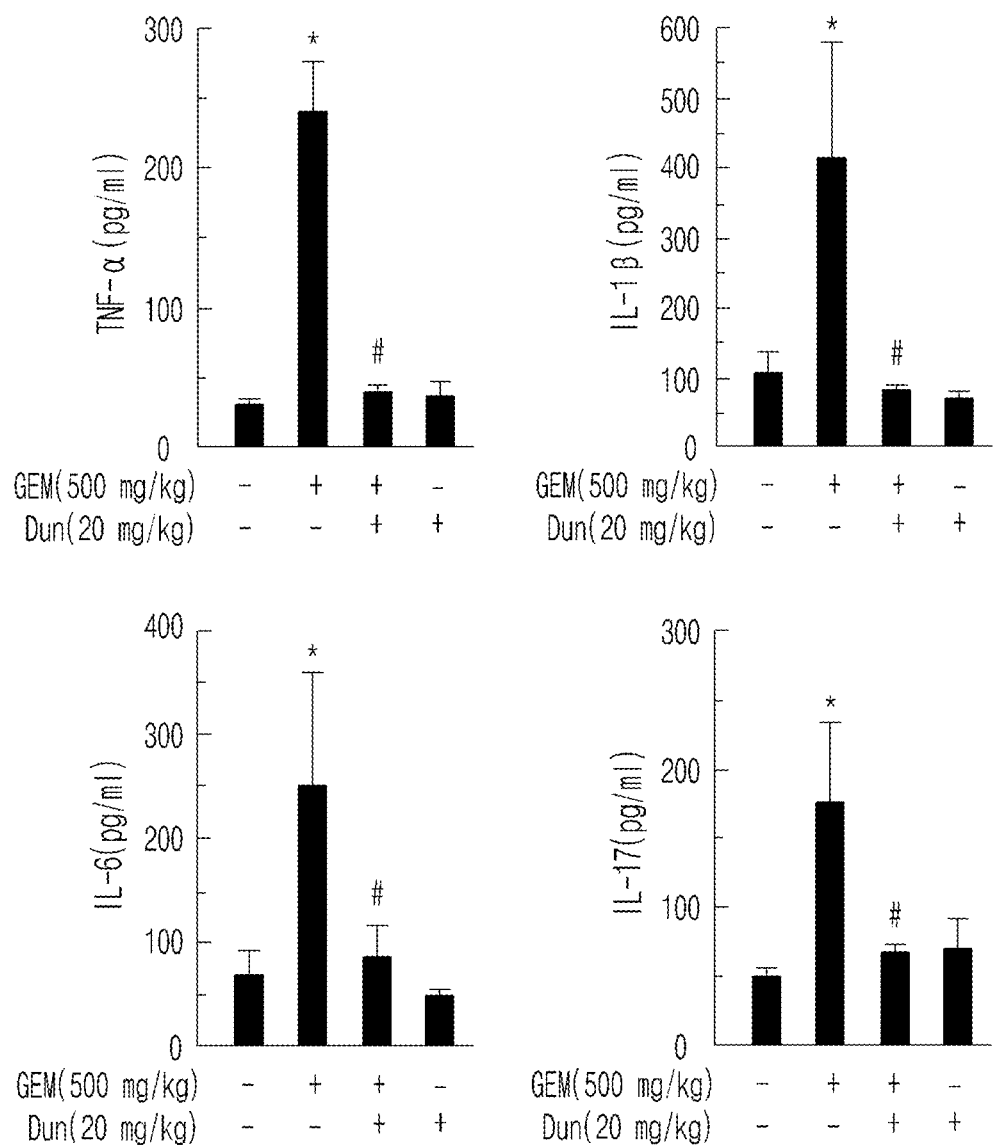

FIG. 2 is a diagram illustrating the regulatory effect of dunnione on inflammatory cytokines (TNF-α, IL-1β, IL-6, and IL-17) in plasma induced by gemcitabine.

Control: PBS treated group; GEM: gemcitabine (500 mg/kg) treated group; GEM+Dun: gemcitabine and dunnione (20 mg/kg) co-treated group; Dun: dunnione (20 mg/kg) treated group.

*p<0.05: comparison of control group and gemcitabine treated group;

p<0.05: comparison of gemcitabine treated group and dunnione treated group.

Figure 3:
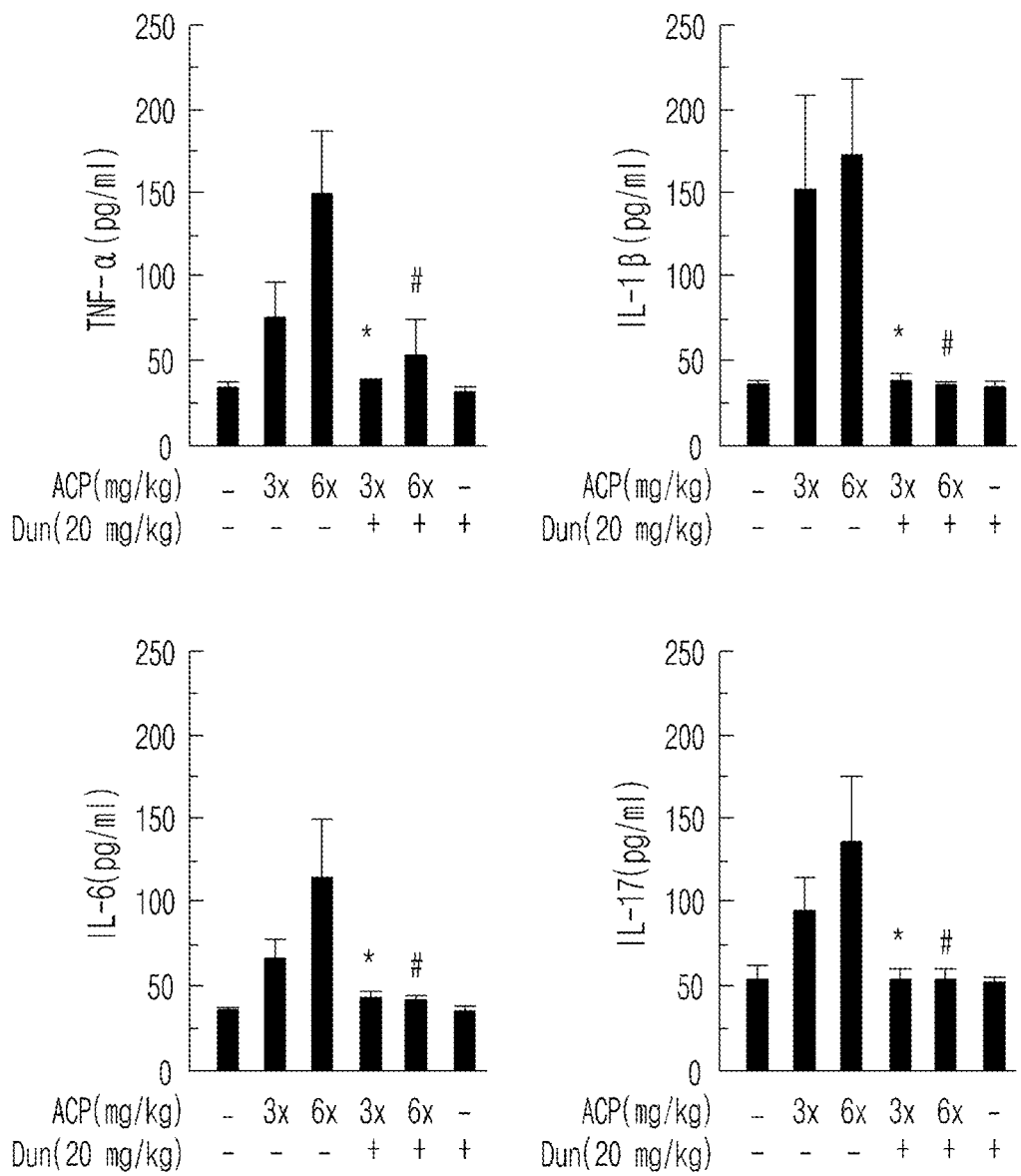

FIG. 3 is a diagram illustrating the regulatory effect of dunnione on inflammatory cytokines (TNF-α, IL-1β, IL-6, and IL-17) in plasma induced by the co-treatment of cyclophosphamide, adriamycin and paclitaxel (ACP) at two different concentrations (3×, 6×ACP).

Control: PBS treated group; 3×ACP: adriamycin (4.62 mg/kg), cyclophosphamide (46.2 mg/kg), and paclitaxel (6.18 mg/kg) co-treated group; 6×ACP: adriamycin (9.24 mg/kg), cyclophosphamide (92.4 mg/kg), and paclitaxel (12.36 mg/kg) treated group; 3×ACP+Dun: 3×ACP and dunnione (20 mg/kg) co-treated group; 6×ACP+Dun: 6×ACP and dunnione (20 mg/kg) co-treated group; Dun: dunnione (20 mg/kg) treated group.

*p<0.05: comparison of 3×ACP treated group and dunnione treated group;

p<0.05: comparison of 6×ACP treated group and dunnione treated group.

Figure 4:
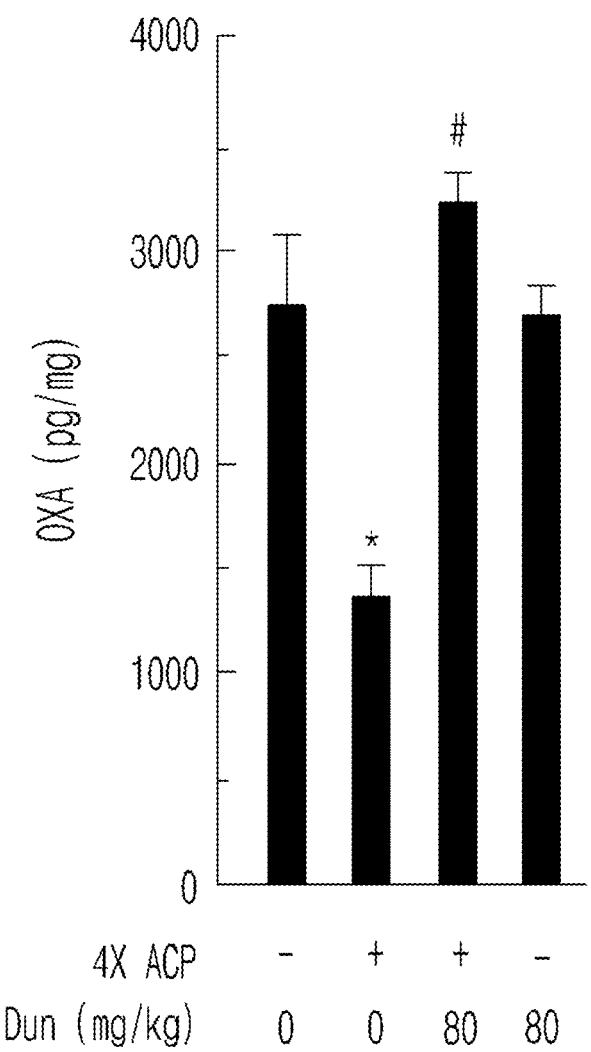

FIG. 4 is a diagram illustrating the regulatory effect of dunnione on the production of orexin protein in the hypothalamus of mice induced by the co-treatment of adriamycin, cyclophosphamide and paclitaxel (4×ACP).

Control: PBS treated group; 4×ACP: 1×ACP adriamycin (1.54 mg/kg), cyclophosphamide (15.4 mg/kg), and paclitaxel (2.06 mg/kg) co-treated group (4 treatments once every 2 days); 4×ACP+Dun: the group treated daily with dunnione at 80 mg/kg 3 days before the ACP treatment; Dun: dunnione (80 mg/kg) treated group.

*p<0.05: comparison of control group and 4×ACP treated group; #p<0.05: comparison of 4×ACP treated group and dunnione treated group.

Figure 5:
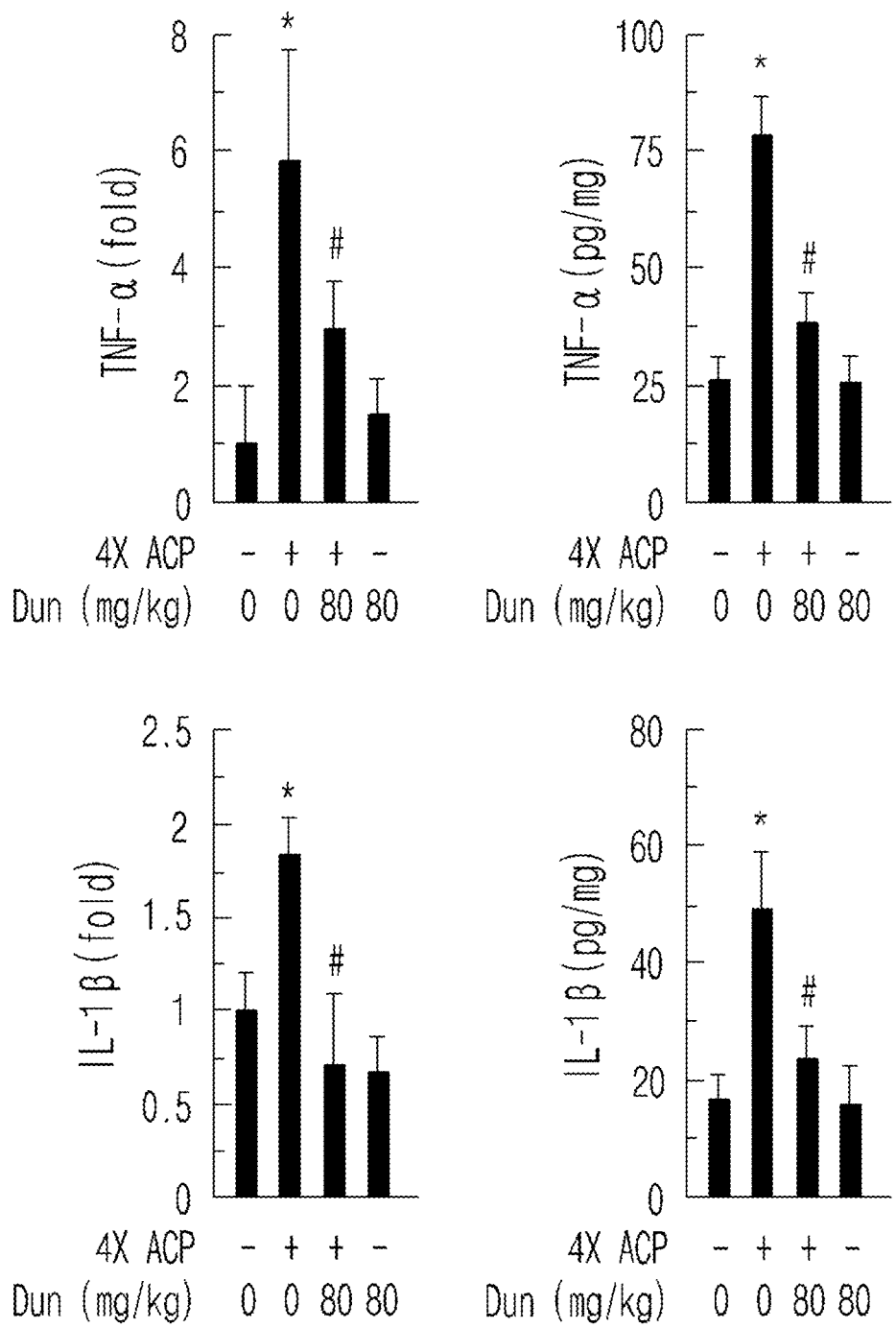

FIG. 5 is a diagram illustrating the regulatory effect of dunnione on the brain inflammatory response induced by the co-treatment of adriamycin, cyclophosphamide and paclitaxel.

Control: PBS treated group; 4×ACP: 1×ACP adriamycin (1.54 mg/kg), cyclophosphamide (15.4 mg/kg), and paclitaxel (2.06 mg/kg) co-treated group (4 treatments once every 2 days); 4×ACP+Dun: the group treated daily with dunnione at 80 mg/kg 3 days before the ACP treatment; Dun: dunnione (80 mg/kg) treated group.

*p<0.05: comparison of control group and 4×ACP treated group;

p<0.05: comparison of 4×ACP treated group and dunnione treated group.

Figure 6:
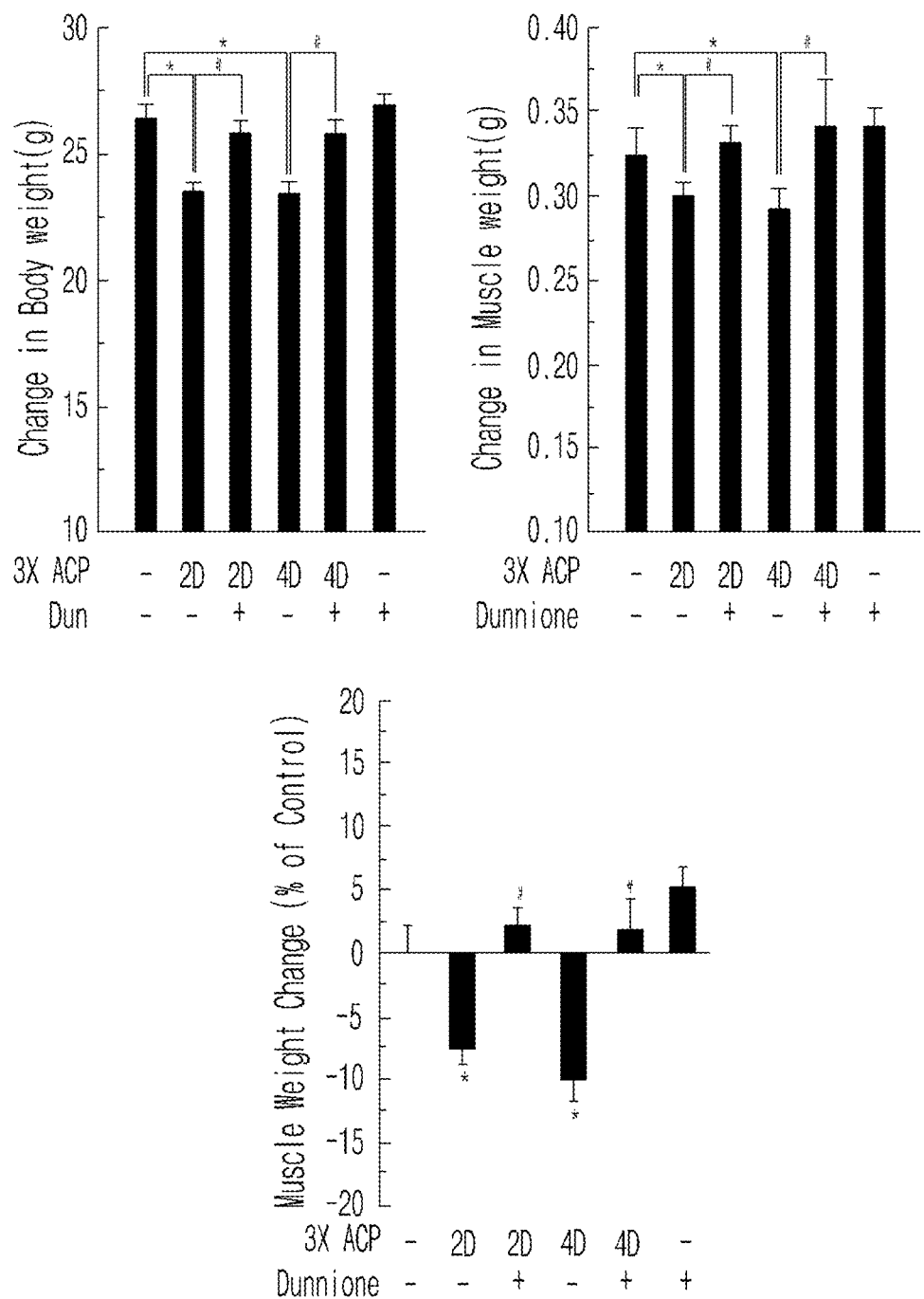

FIG. 6 is a diagram illustrating the effect of dunnione on the muscle loss model induced by the co-treatment of adriamycin, cyclophosphamide and paclitaxel (3×ACP).

Control: PBS treated group; 3×ACP 2D: the group co-treated with adriamycin (4.62 mg/kg), cyclophosphamide (46.2 mg/kg), and paclitaxel (6.18 mg/kg) for 2 days; 3×ACP 2D+Dun: the group treated daily with dunnione (20 mg/kg) for 3 days and then treated with 3×ACP for 2 days; 3×ACP 4D: the group co-treated with adriamycin (4.62 mg/kg), cyclophosphamide (46.2 mg/kg), and paclitaxel (6.18 mg/kg) for 4 days; 3×ACP 2D+Dun: the group treated with dunnione (20 mg/kg) for 3 days and then treated with 3×ACP for 4 days; Dun: dunnione (20 mg/kg) treated group.

*p<0.05: comparison of control group and 3×ACP treated group;

p<0.05: comparison of 3×ACP treated group and dunnione treated group.

Figure 7:
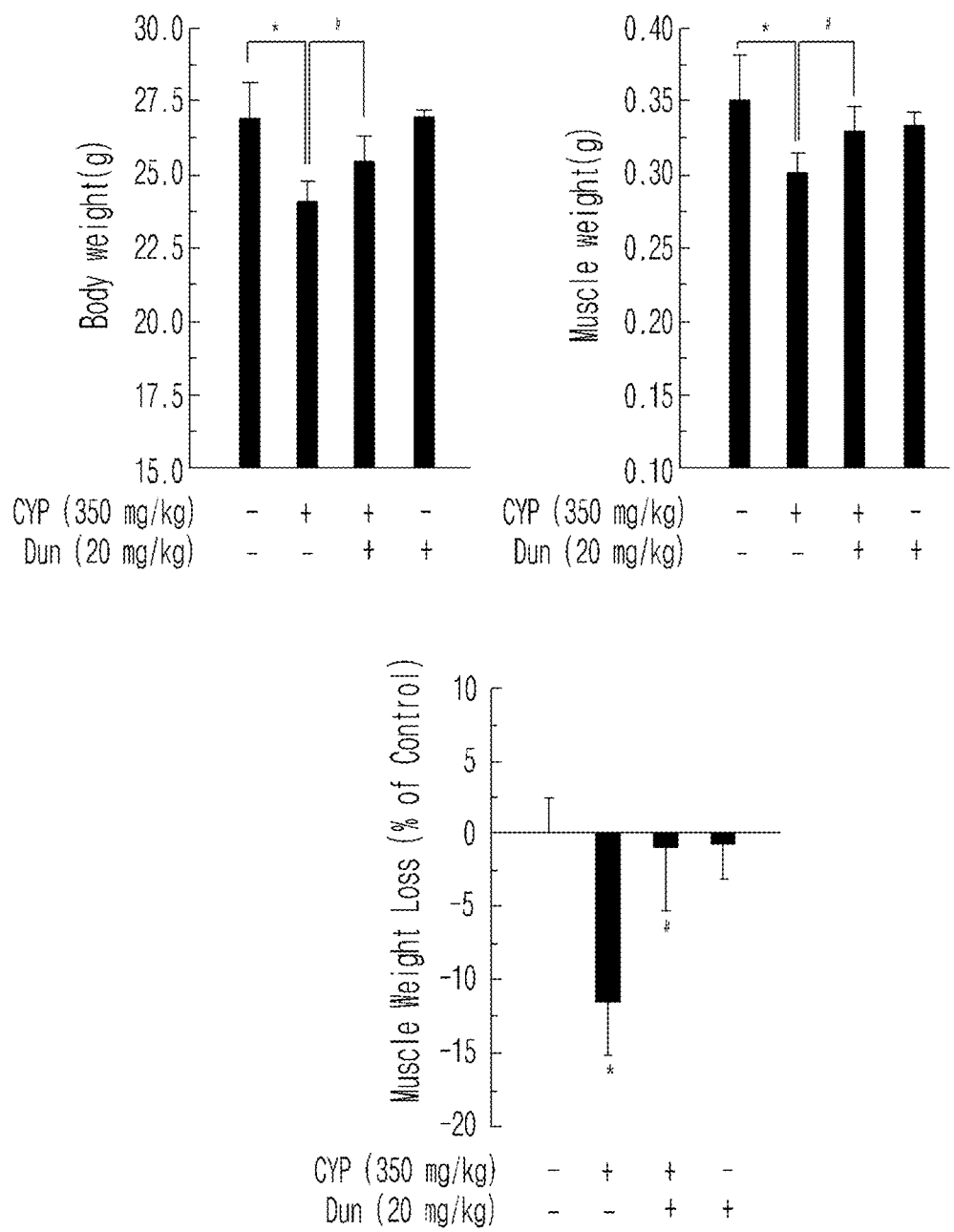

FIG. 7 is a diagram illustrating the effect of dunnione on the muscle loss model induced by cyclophosphamide.

Control: PBS treated group; CYP: cyclophosphamide (150 mg/kg+200 mg/kg) treated group; CYP+Dun: the group treated daily with dunnione (20 mg/kg) 3 days before the cyclophosphamide treatment; Dun: dunnione (20 mg/kg) treated group.

*p<0.05: comparison of control group and CYP treated group;

p<0.05: comparison of CYP treated group and dunnione treated group.

Figure 8:
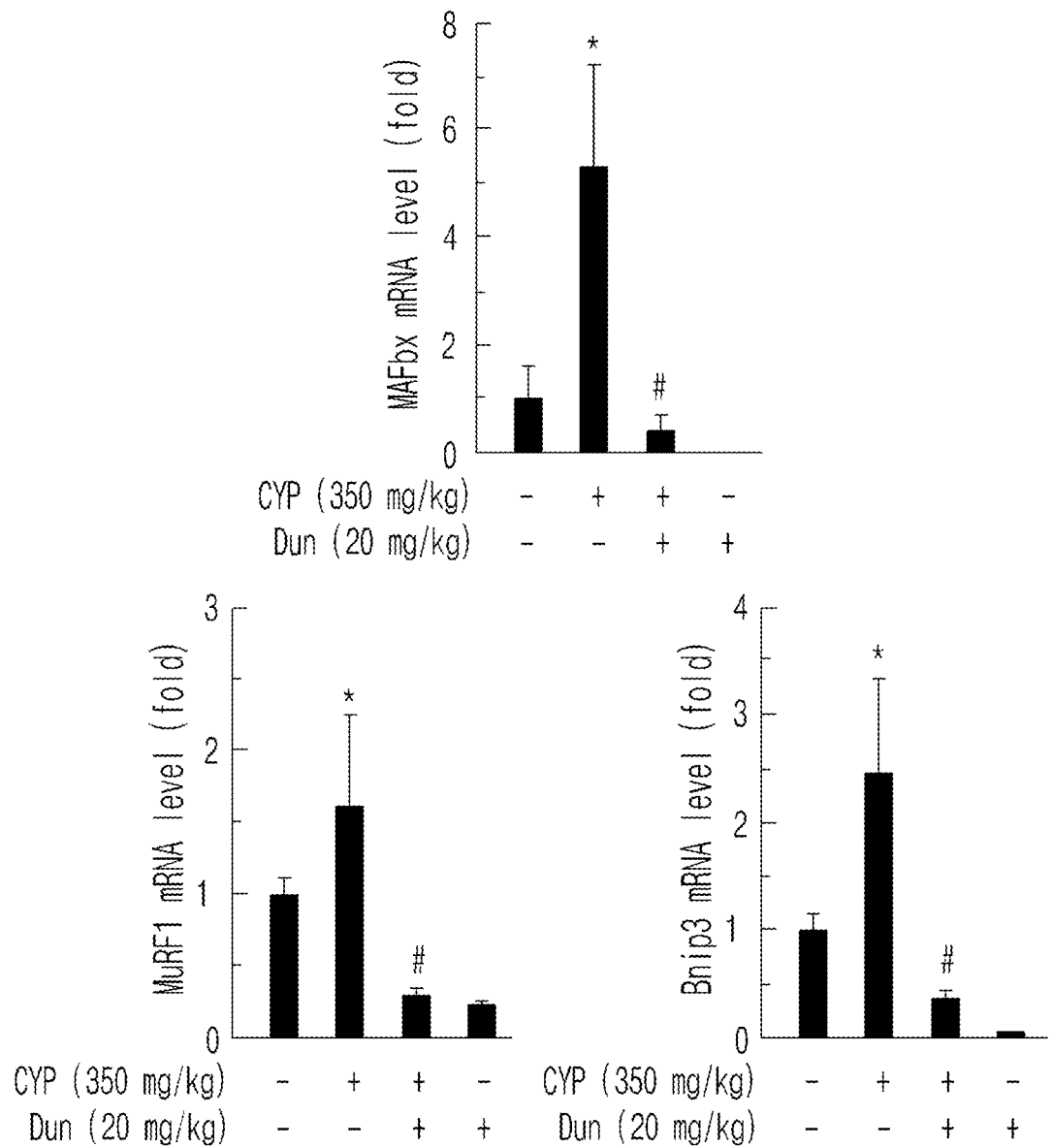

FIG. 8 is a diagram illustrating the regulatory effect of dunnione on the muscle loss related gene in the muscle loss model induced by cyclophosphamide.

Control: PBS treated group; CYP: cyclophosphamide (150 mg/kg+200 mg/kg) treated group; CYP+Dun: the group treated daily with dunnione (20 mg/kg) 3 days before the cyclophosphamide treatment; Dun: dunnione (20 mg/kg) treated group.

*p<0.05: comparison of control group and CYP treated group;

p<0.05: comparison of CYP treated group and dunnione treated group.

Figure 9A:
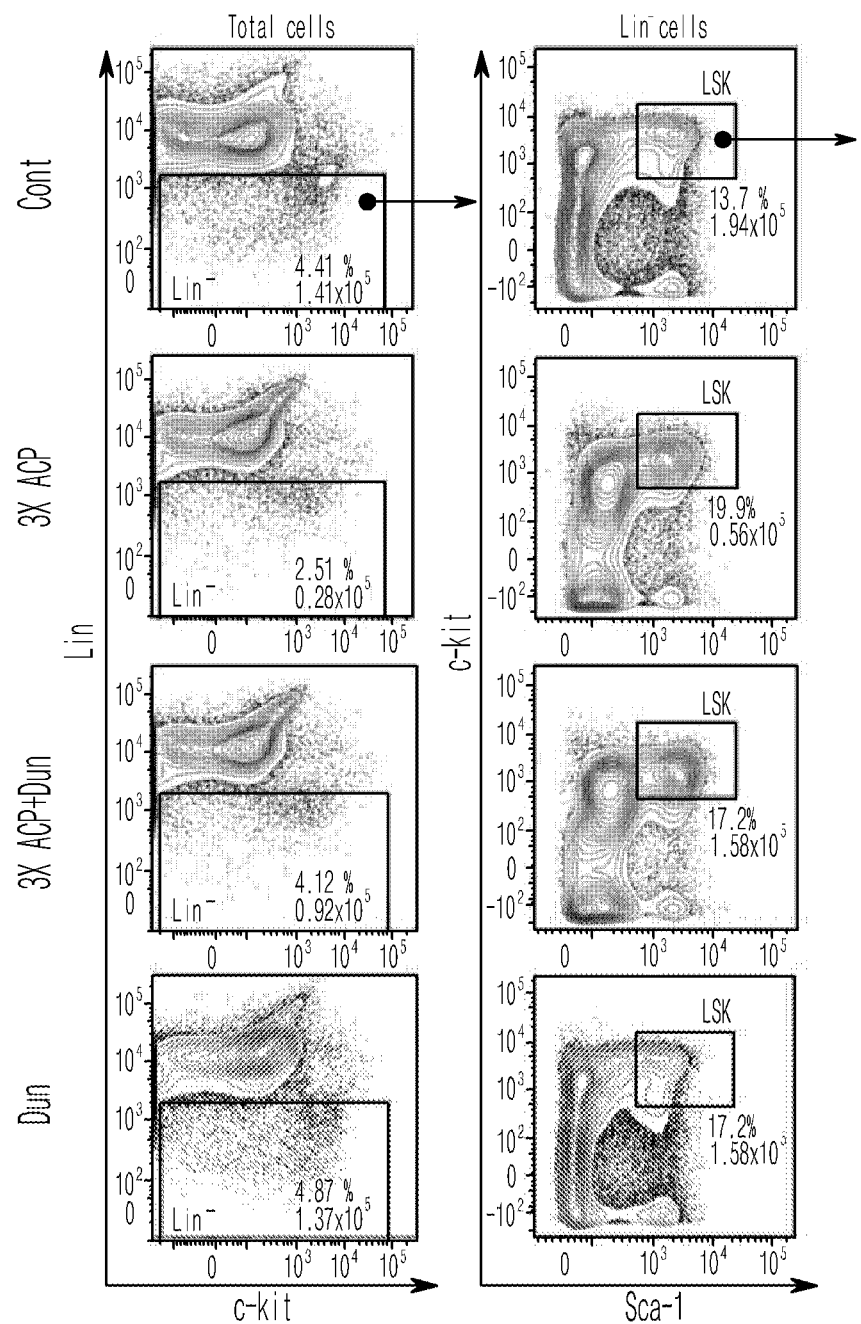

FIG. 9a is a diagram illustrating the results of flow cytometry performed to investigate the effect of dunnione on the reduction of bone marrow cells and hematopoietic stem/progenitor cells induced by the co-treatment of adriamycin, cyclophosphamide and paclitaxel, wherein Lin-cells among total cells were investigated and LSK (Lin-Sca-1+Kit+) cells in Lin-cells were investigated. This experiment is shown continuously in FIG. 9b.

Figure 9B:
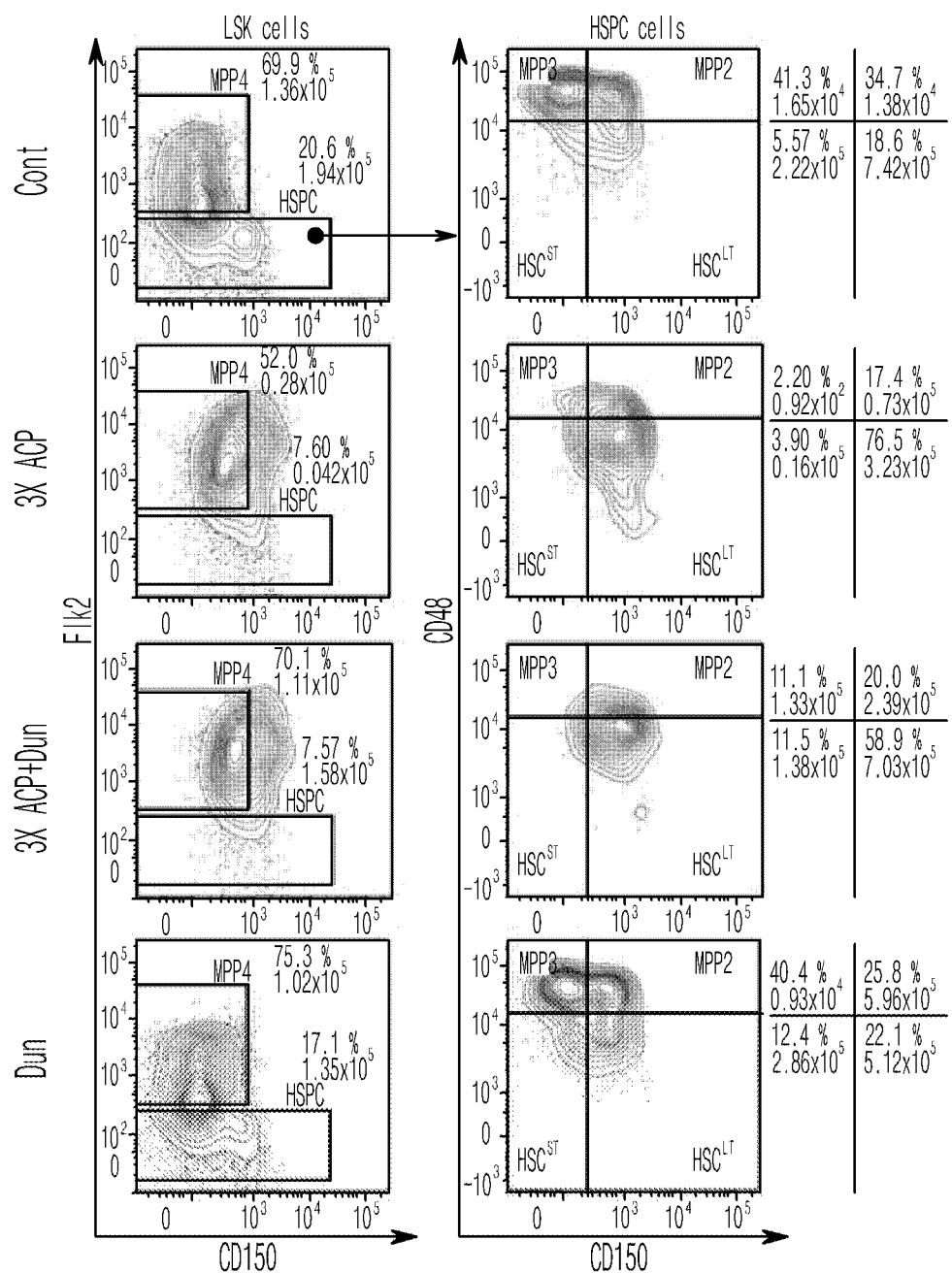

FIG. 9b is a diagram illustrating the investigation of multipotent progenitor-4 (MPP4) and hematopoietic stem/progenitor cells (HSPC) in LSK (Lin-Sca-1+Kit+) above and further investigation of HSCLT (long-term hematopoietic stem cells), HSCST (short-term hematopoietic stem cells) and multipotent progenitor-2,-3 (MPP2 and MPP3).

Cont: PBS treated group; 3×ACP: adriamycin (4.62 mg/kg), cyclophosphamide (46.2 mg/kg) and paclitaxel (6.18 mg/kg) co-treated group; 3×ACP+Dun: the group treated daily with dunnione at 20 mg/kg 3 days before the 3×ACP treatment.

MPP2: progenitor cells which are finally differentiated into megakaryocytes and red blood cells; MPP3: progenitor cells which are finally differentiated into polynuclear cells and mononuclear cells; MPP4: progenitor cells which are finally differentiated into lymphocytes.

Figure 10:
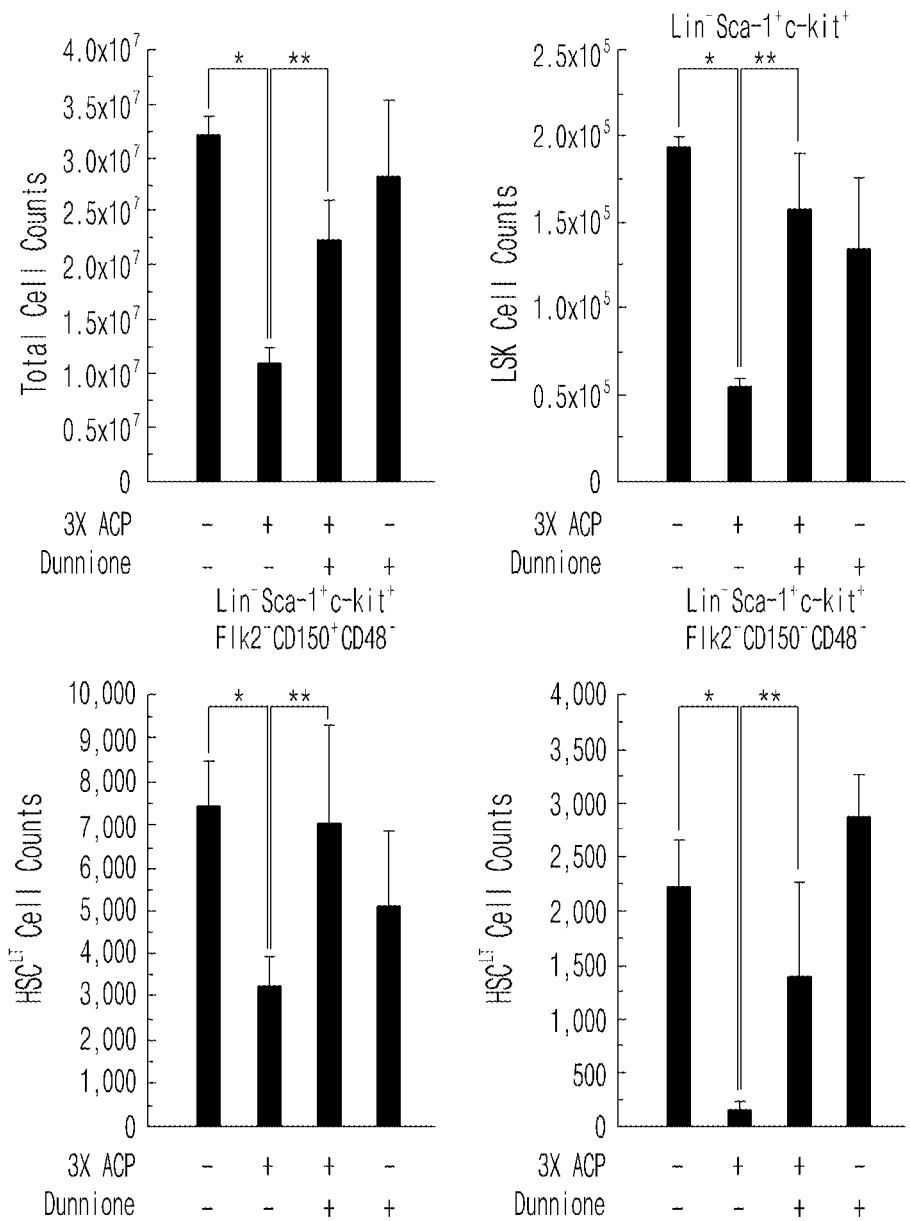

FIG. 10 is a diagram illustrating the investigation of the protective effect of dunnione on the reduction of bone marrow cells and hematopoietic stem/progenitor cells induced by the co-treatment of adriamycin, cyclophosphamide and paclitaxel, confirmed by comparing the absolute cell number.

Total cell counts: total number of cells obtained from bone marrow; LSK cell counts; Sca-1 and c-Kit positive cells before differentiation; HSCLT: Lin-Sca-1+c-Kit+Flk2-CD150+CD48-long-term hematopoietic stem cells; HSCST: Lin-Sca-1+c-Kit+Flk2-CD150-CD48-short-term hematopoietic stem cells.

Cont: PBS treated group; 3×ACP: adriamycin (4.62 mg/kg), cyclophosphamide (46.2 mg/kg) and paclitaxel (6.18 mg/kg) co-treated group; 3×ACP+Dun: the group treated daily with dunnione at 20 mg/kg 3 days before the 3×ACP treatment.
  *p<0.05: comparison of control group and 3×ACP treated group;
  ** p<0.05: comparison of 3×ACP treated group and dunnione treated group.

Figure 11:
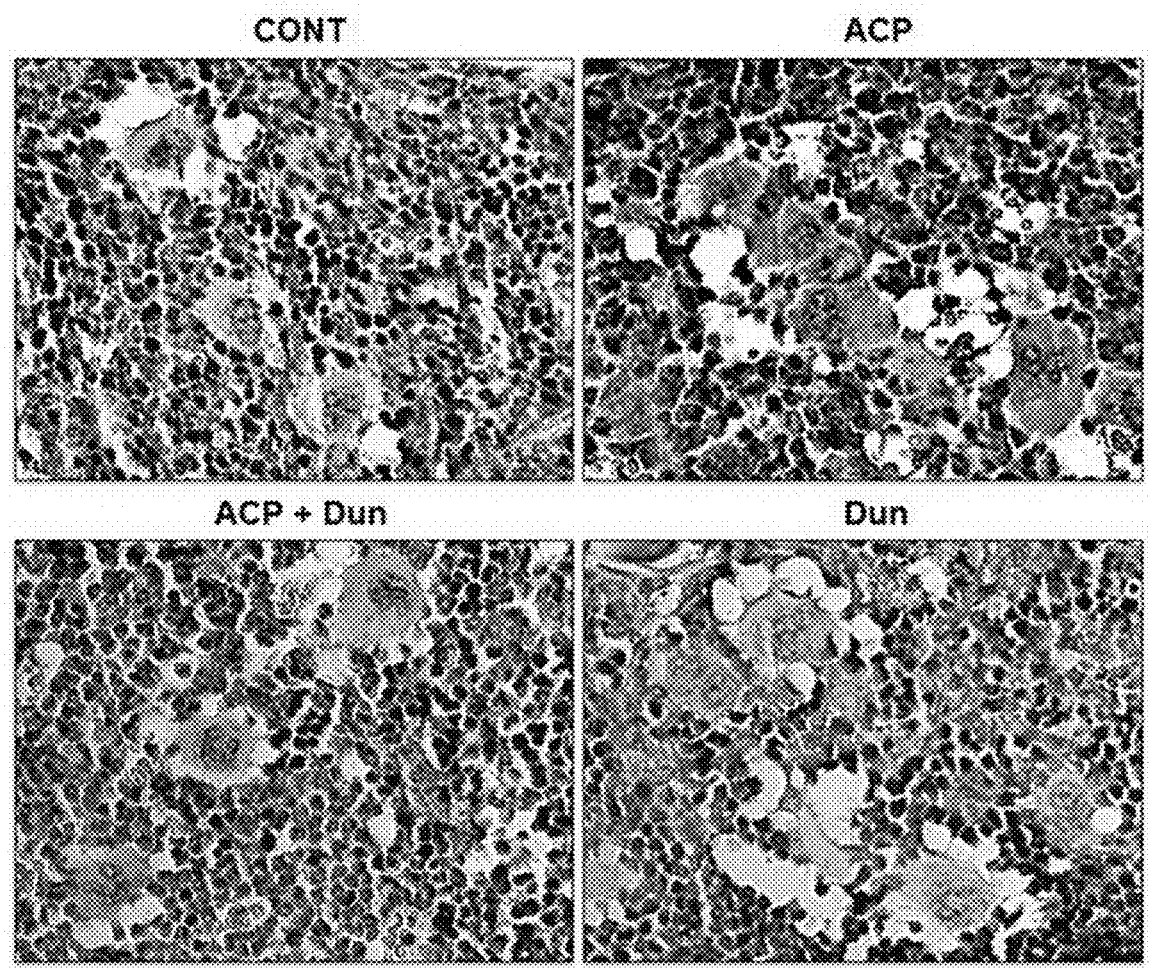

FIG. 11 is a diagram illustrating the effect of dunnione on the expression of TNF-α in the femur induced by the co-treatment of adriamycin, cyclophosphamide and paclitaxel.
  CONT: PBS treated group; ACP: 1×ACP adriamycin (1.54 mg/kg), cyclophosphamide (15.4 mg/kg), and paclitaxel (2.06 mg/kg) co-treated group (4 treatments once every 2 days); ACP+Dun: the group treated daily with dunnione at 80 mg/kg 3 days before the ACP treatment; Dun: dunnione (80 mg/kg) treated group.

Figure 12:
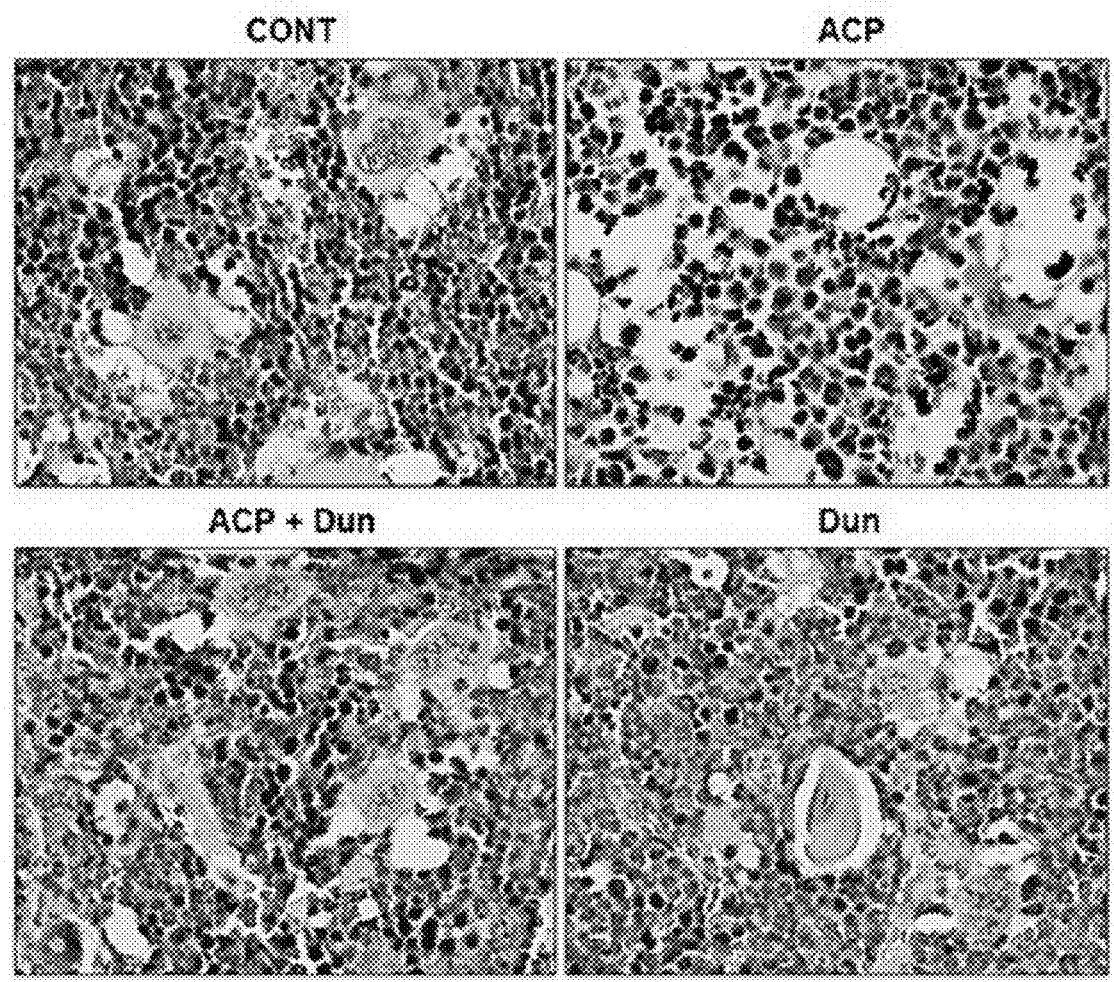

FIG. 12 is a diagram illustrating the effect of dunnione on the inflow of macrophages into the femur induced by the co-treatment of adriamycin, cyclophosphamide and paclitaxel.
  CONT: PBS treated group; ACP: 1×ACP adriamycin (1.54 mg/kg), cyclophosphamide (15.4 mg/kg), and paclitaxel (2.06 mg/kg) co-treated group (4 treatments once every 2 days); ACP+Dun: the group treated daily with dunnione at 80 mg/kg 3 days before the ACP treatment; Dun: dunnione (80 mg/kg) treated group.

Figure 13:
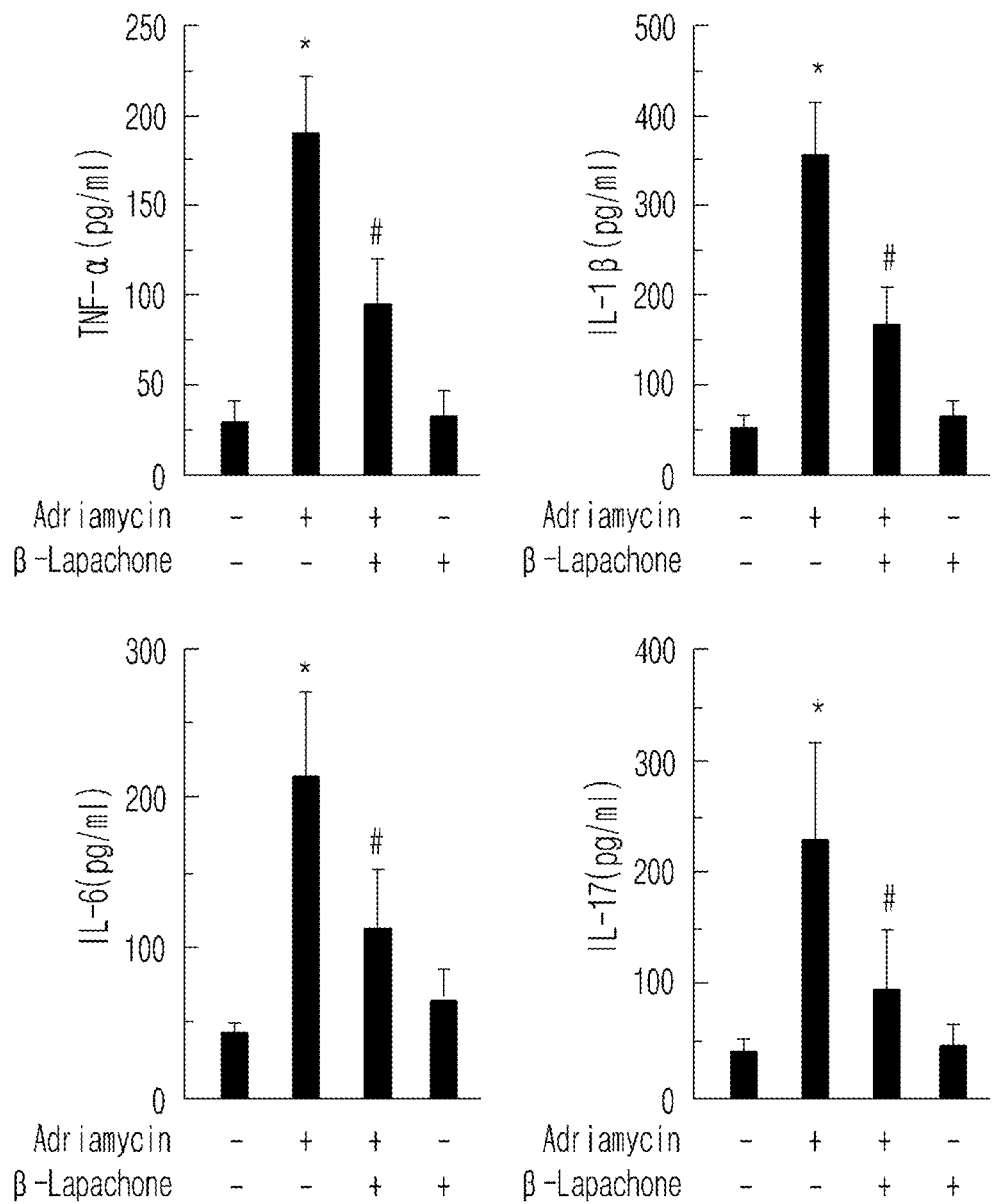

FIG. 13 is a diagram illustrating the regulatory effect of β-lapachone on inflammatory cytokines (TNF-α, IL-1B, IL-6, and IL-17) in plasma induced by adriamycin.
  Control: PBS treated group; Adriamycin: adriamycin (4 mg/kg×3) treated group; Adriamycin+β-Lapachone: adriamycin and β-lapachone (20 mg/kg) co-treated group; β-Lapachone: β-lapachone (20 mg/kg) treated group.
  *p<0.05: comparison of control group and adriamycin treated group;
  #p<0.05: comparison of adriamycin treated group and β-lapachone treated group.

Figure 14:
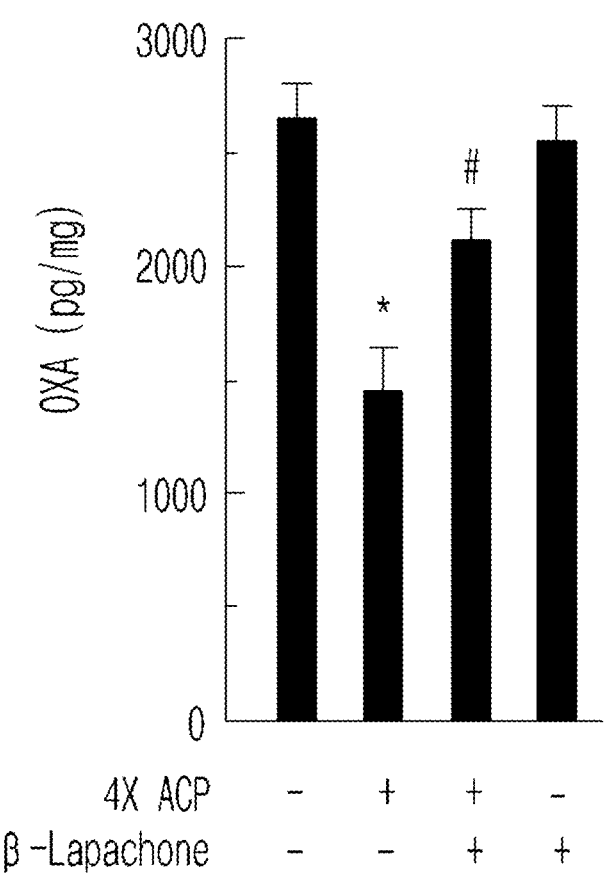

FIG. 14 is a diagram illustrating the regulatory effect of β-lapachone on the production of orexin protein in the hypothalamus of mice induced by the co-treatment of adriamycin, cyclophosphamide and paclitaxel (4×ACP).
  Control: PBS treated group; 4×ACP: 1×ACP adriamycin (1.54 mg/kg), cyclophosphamide (15.4 mg/kg), and paclitaxel (2.06 mg/kg) co-treated group (4 treatments once every 2 days); 4×ACP+β-Lapachone: the group treated daily with β-lapachone at 20 mg/kg 3 days before the ACP treatment; β-Lapachone: β-lapachone (20 mg/kg) treated group.
  *p<0.05: comparison of control group and 4×ACP treated group;
  #p<0.05: comparison of 4×ACP treated group and β-lapachone treated group.

Figure 15:
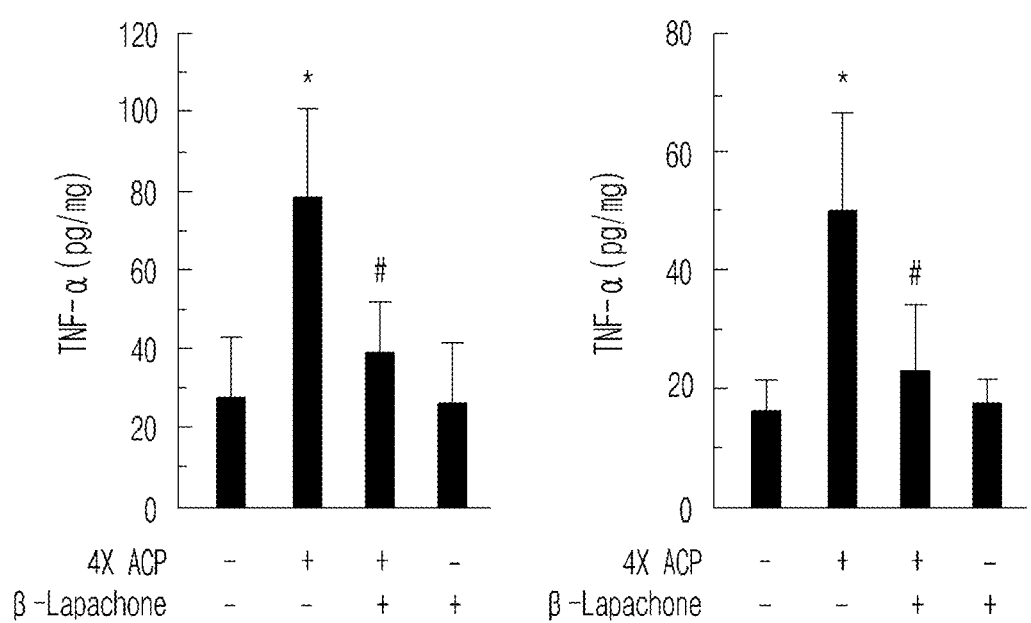
Figure 16:
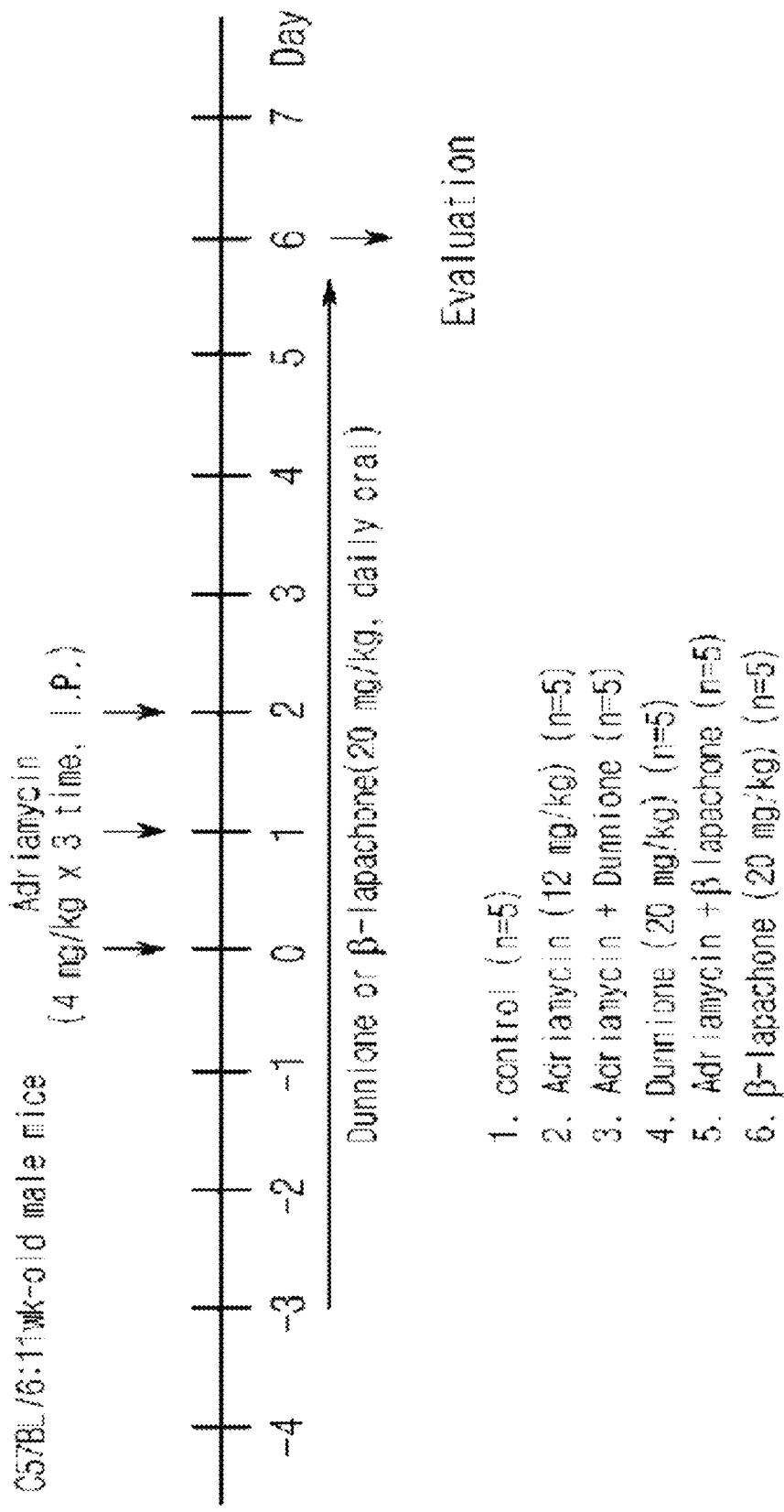
Figure 17:
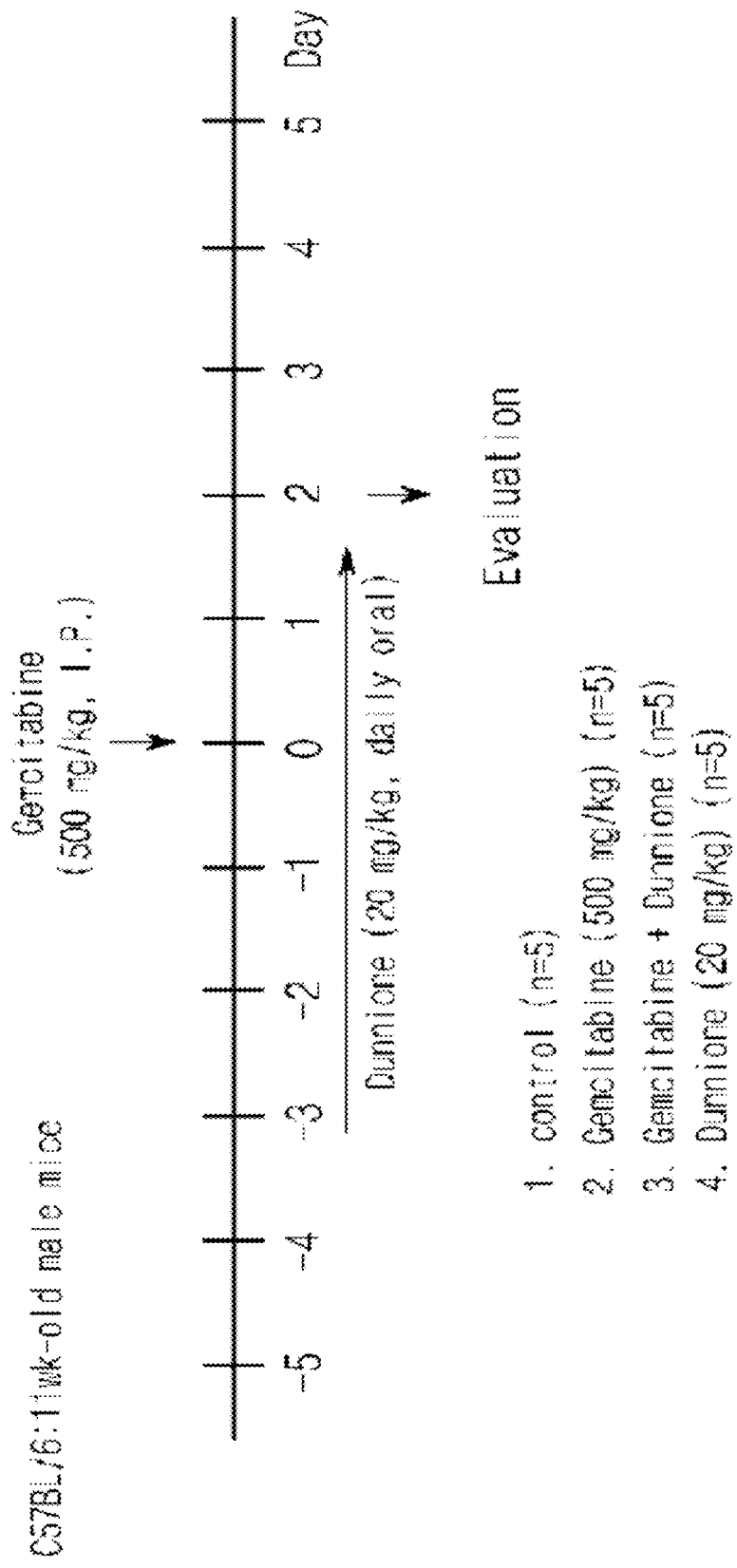
Figure 18:
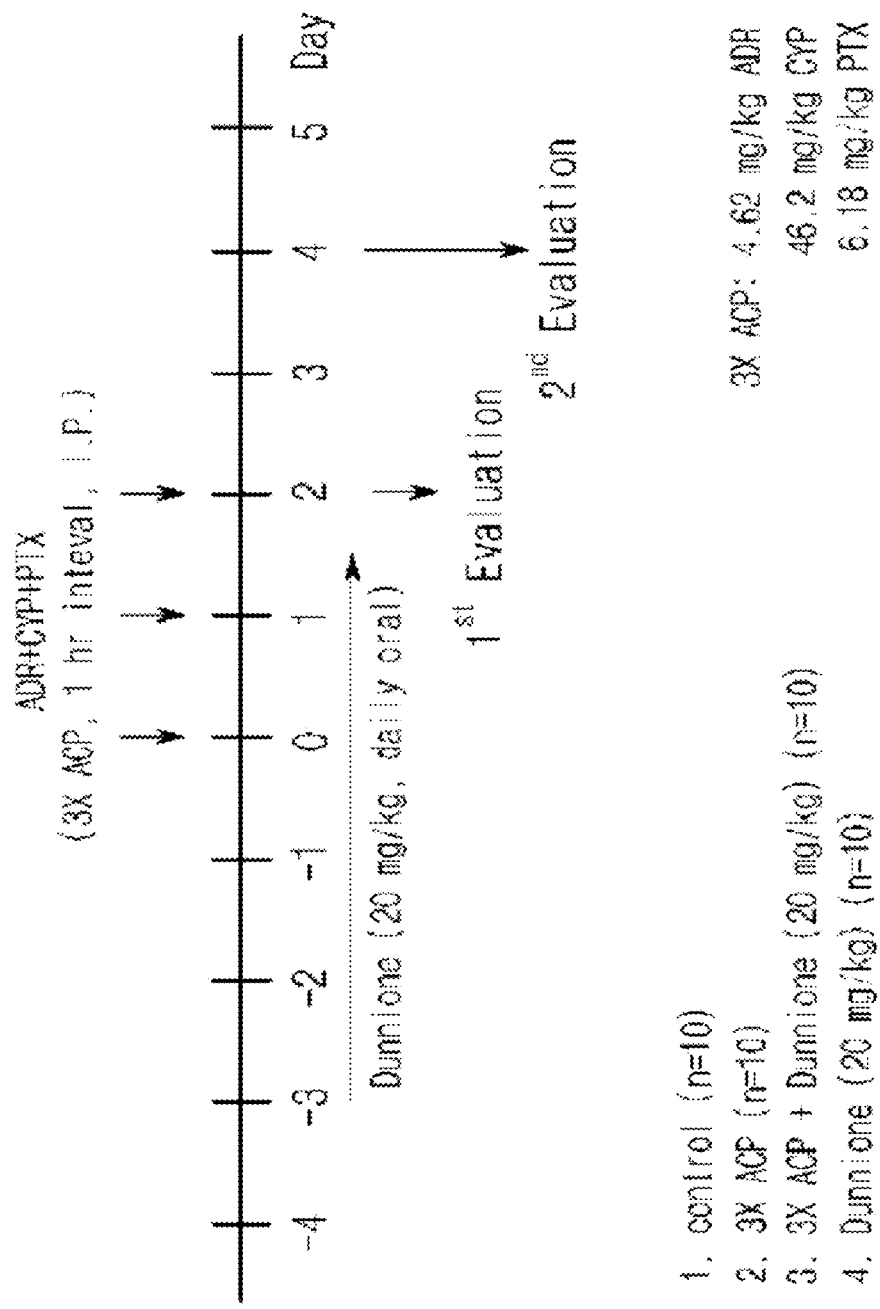
Figure 19:
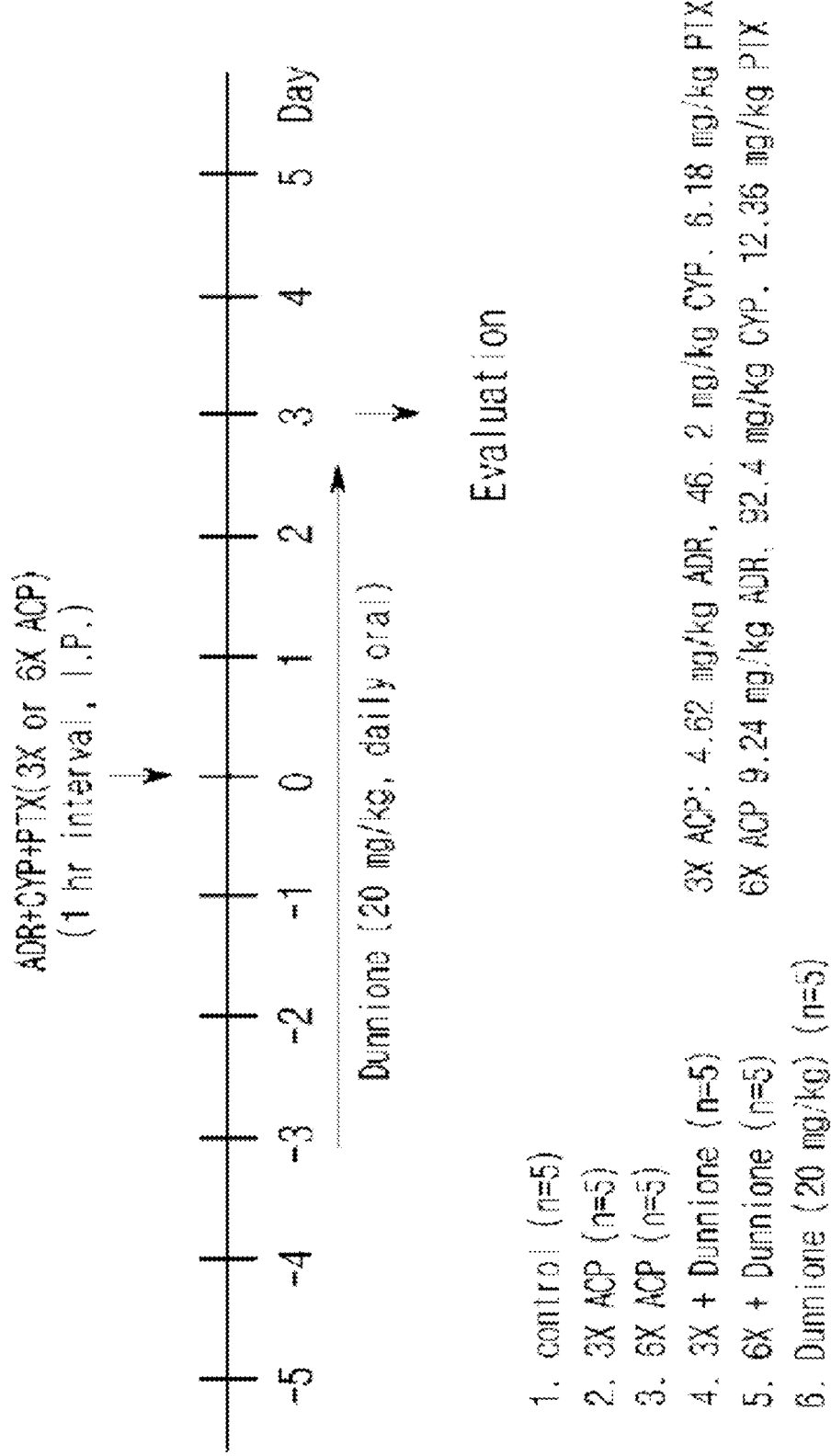
Figure 20:
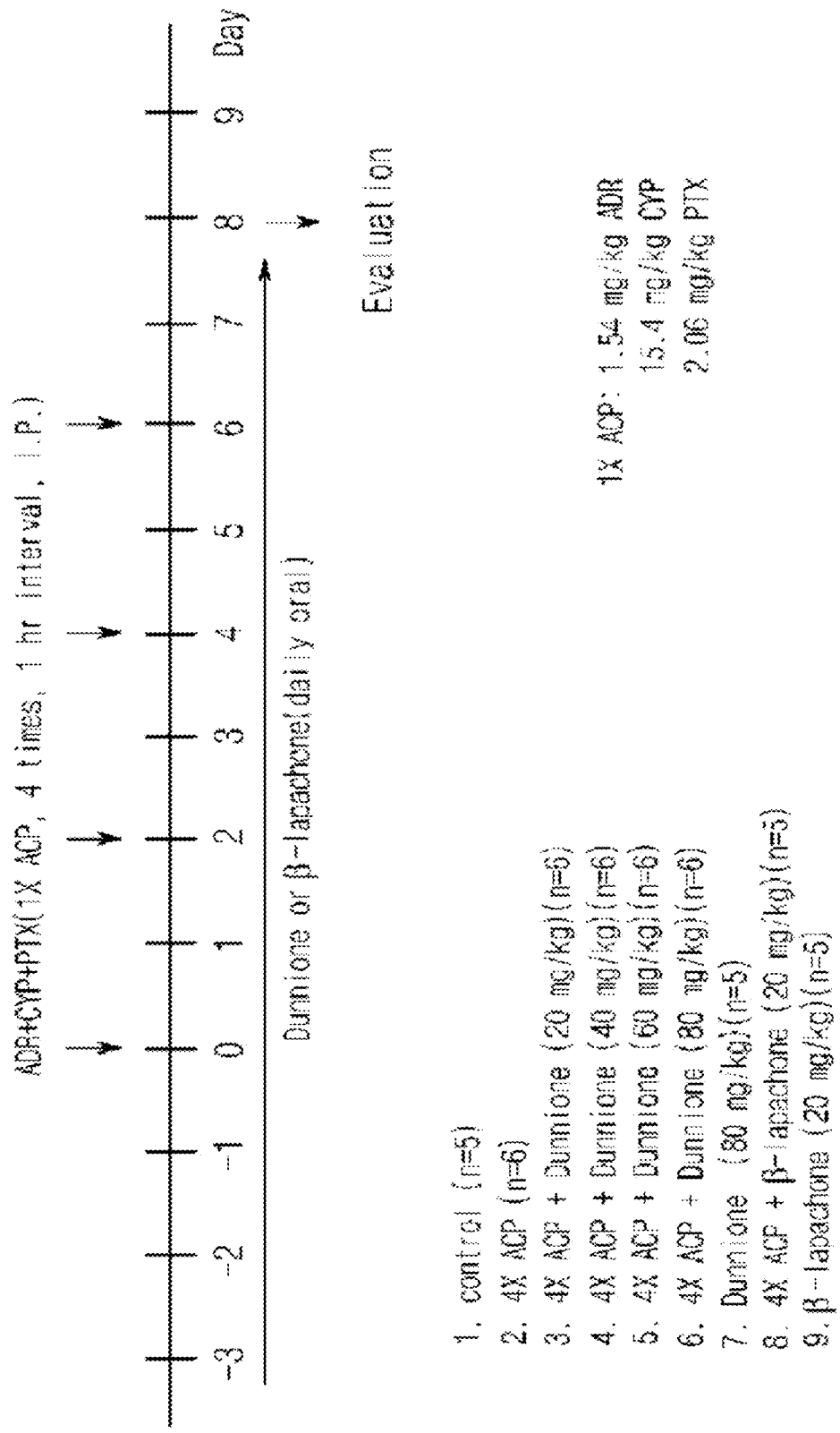
Figure 21:
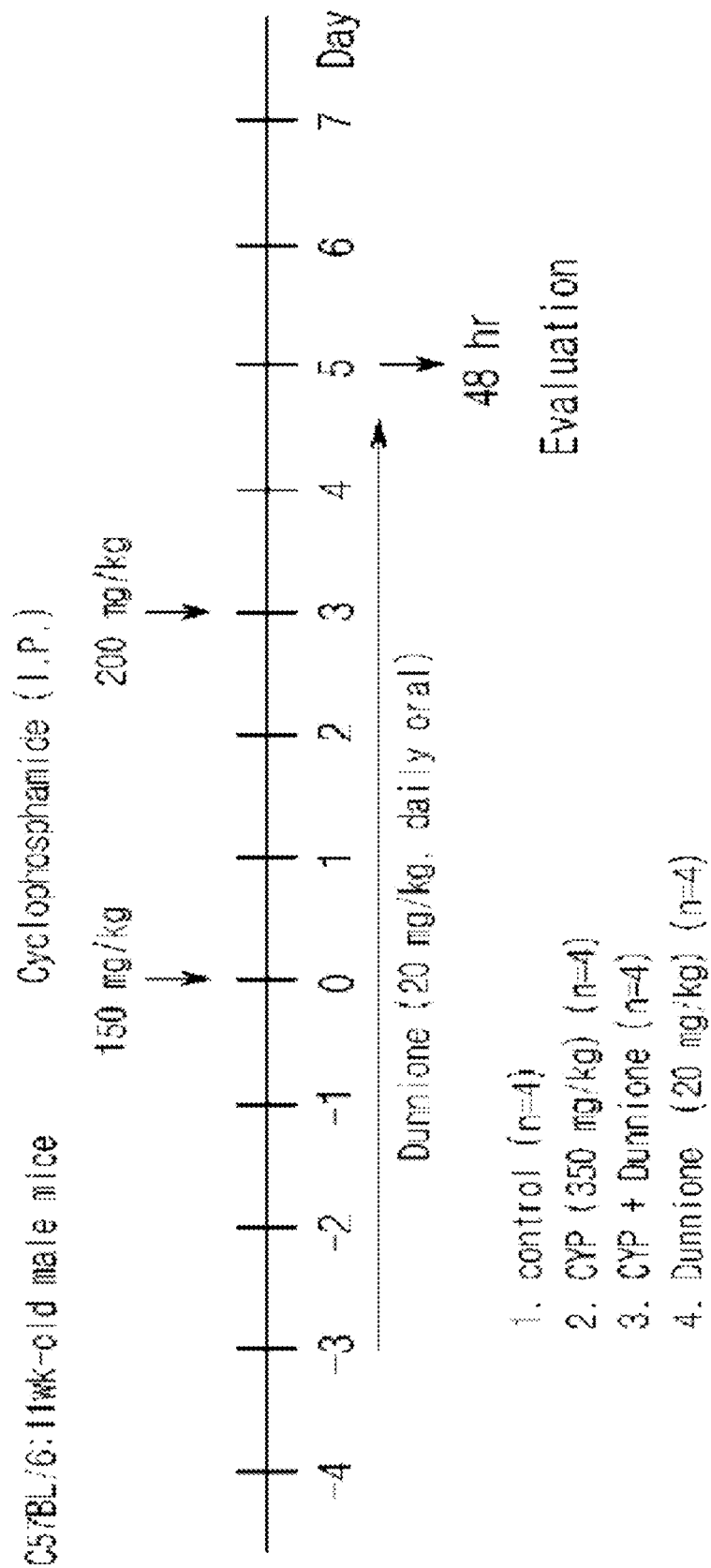
Figure 22:
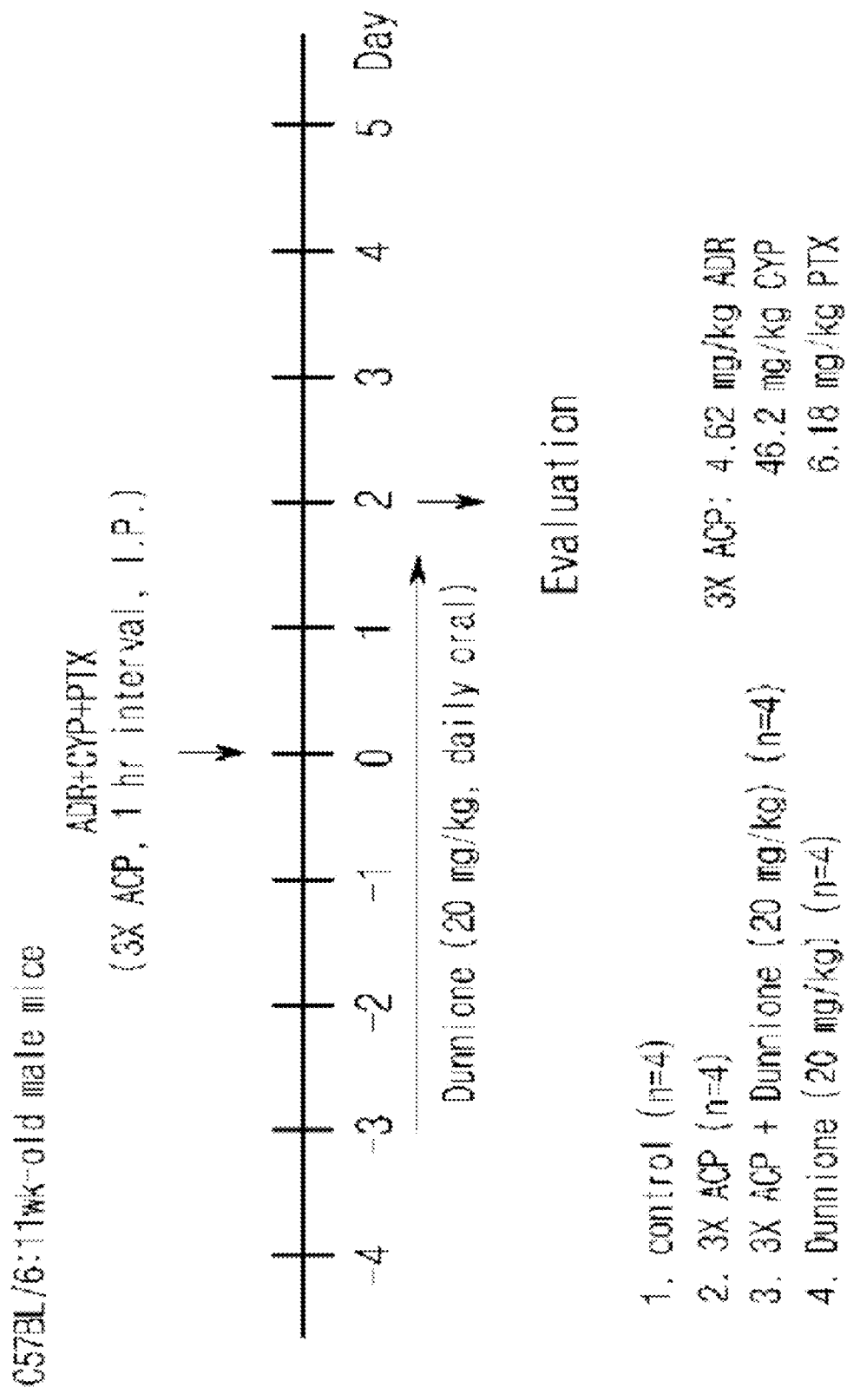

FIG. 15 is a diagram illustrating the regulatory effect of β-lapachone on the brain inflammatory response induced by the co-treatment of adriamycin, cyclophosphamide and paclitaxel (ACP).
  Control: PBS treated group; 4×ACP: 1×ACP adriamycin (1.54 mg/kg), cyclophosphamide (15.4 mg/kg), and paclitaxel (2.06 mg/kg) co-treated group (4 treatments once every 2 days); 4×ACP+β-Lapachone: the group treated daily with β-lapachone at 20 mg/kg 3 days before the ACP treatment; β-Lapachone: β-lapachone (20 mg/kg) treated group.
  *p<0.05: comparison of control group and 4×ACP treated group;
  #p<0.05: comparison of 4×ACP treated group and β-lapachone treated group.

FIGS. 16-22 show diagrams illustrating the dosing schedules employed in the animal experiments.

DESCRIPTION OF THE PREFERRED EMBODIMENTS

Hereinafter, the terms used in this invention are described.

The term 'pharmaceutically acceptable salt' indicates a formulation of a compound which does not cause serious irritation to the organism to which the compound is administered and does not damage the biological activity and properties of the compound. The pharmaceutical salt includes acid addition salts formed by acids which form non-toxic acid addition salts containing pharmaceutically acceptable anions, for example inorganic acids such as hydrochloric acid, sulfuric acid, nitric acid, phosphoric acid, hydrobromic acid and hydroiodic acid, organic carboxylic acids such as tartaric acid, formic acid, citric acid, acetic acid, trichloroacetic acid, trifluoroacetic acid, gluconic acid, benzoic acid, lactic acid, fumaric acid, maleic acid and salicinic acid, and sulfonic acids such as methanesulfonic acid, ethanesulfonic acid, benzenesulfonic acid and p-toluenesulfonic acid. The pharmaceutically acceptable carboxylic acid salts include metal salts or alkaline earth metal salts formed with lithium, sodium, potassium, calcium and magnesium, amino acid salts such as lysine, arginine and guanidine, and organic salts such as dicyclohexylamine, N-methyl-D-glucamine, tris(hydroxymethyl)methylamine, diethanolamine, choline and triethylamine. The compounds represented by formula 1 and formula 2 of the present invention can be converted into salts by the conventional method.

The term 'prodrug' indicates a material that is transformed into its parent drug in vivo. Prodrugs are often used because they are easier to administer than their parent drugs. For example, the oral administration of prodrugs secures bioactivity, whereas parent drugs may not. The solubility of prodrugs in a pharmaceutical composition is higher than that of parent drugs. For example, even though the water solubility of prodrug is not beneficial for mobility, the prodrug can be a compound that can be administered as an ester (prodrug) which can be hydrolyzed into active carboxylic acid through metabolism and can pass through cell membrane easily in cells wherein the water solubility is beneficial thereby. Another example of prodrug is a short peptide (polyamino acid) binding to an acid group that can be transformed in order for the peptide to show the active site.

The term 'solvate' indicates the compound of the present invention or its salts containing stoichiometric or non-stoichiometric amount of solvents linked by non-covalent intermolecular force. Preferred solvents are volatile solvents, non-toxic solvents, and/or solvents suitable for administration to humans, and when the solvent is water, it is hydrate.

The term 'isomer' indicates the compound of the present invention or its salts having the same chemical or molecular formula but having different optical or steric structure.

Unless indicated otherwise, the term 'compound represented by formula 1 or formula 2' indicates the concept containing all of the compound itself, pharmaceutically acceptable salts thereof, prodrugs thereof, solvates thereof and isomers thereof.

In addition, the term 'therapeutically effective amount' indicates the amount of an active ingredient to be administered which efficiently reduces or relieves one or more symptoms of a target disease or efficiently delays the development of symptoms or clinical markers of a target disease for the prevention. Therefore, the therapeutically effective amount indicates the amount of an active ingredient that can show (1) the effect of reversing the progress speed of disease, (2) the effect of inhibiting any further progress of disease and/or (3) the effect of relieving (preferably eliminating) one or more symptoms accompanied by disease. The therapeutically effective amount of a compound can be determined by testing the compound in the well-informed in vivo and in vitro disease model systems.

The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The naphthoquinone-based compound, the pharmaceutically acceptable salt thereof, the prodrug thereof, the solvate thereof or the isomer thereof of the present invention can be administered by parenterally and the parenteral administration includes subcutaneous injection, intravenous injection, intramuscular injection and intrathoracic injection. To prepare the naphthoquinone-based compound, the pharmaceutically acceptable salt thereof, the prodrug thereof, the solvate thereof or the isomer thereof of the present invention as a formulation for parenteral administration, the naphthoquinone-based compound, the pharmaceutically acceptable salt thereof, the prodrug thereof, the solvate thereof or the isomer thereof of the present invention is mixed with a stabilizer or a buffering agent to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the composition of the present invention can be determined according to age, weight, gender, administration form, health condition, and severity of a disease. The dosage of the composition is 0.001~2,000 mg/60 kg per day and preferably 0.01~1,000 mg/60 kg per day, and administration frequency is once a day or preferably a few times a day according to the judgment of a doctor or a pharmacist. The pharmaceutical composition of the present invention can contain the naphthoquinone-based compound by 0.01~100 weight %.

In a preferred embodiment of the present invention, the amorphous structure can be formed in the course of producing the active material into fine particles. The fine particles can be prepared by a spray drying method of an active material, a melting method for forming a polymer and a melt, a coprecipitation method for forming a coprecipitate with a polymer by dissolving in a solvent, a clathrate forming method, and a solvent volatilization method. Preferably, a spray drying method can be used herein. In the meantime, fine atomization of the active material through the mechanical pulverization method contributes to improve the solubility due to the large specific surface area, even though the structure is not an amorphous structure, that is, a crystalline crystal structure or a semi-crystalline crystal structure, and as a result it can help the improvement of the dissolution rate and the absorption rate in the body.

The spray drying method is a method of preparing fine particles by dissolving the active material in a proper solvent and then drying thereof while spraying. In the course of performing spray-drying, the crystallinity of the naphthoquinone-based compound itself is lost considerably, resulting in the amorphous form. As a result, a spray dried product of fine particles is obtained.

The mechanical pulverization method is a method of pulverizing the active material into fine particles by pressing the active material with a strong physical force, for which a pulverizing process such as a jet mill, a ball mill, a vibration mill, a hammer mill, etc. can be used. Preferably, a jet mill capable of performing pulverization under the condition of 40° C. or lower using air pressure can be used.

Regardless of the crystal structure, as the particle size of the fine particle type active material decreases, the dissolution rate and solubility increase due to the increase of the specific surface area. However, if the particle size is too small, it is not easy to produce fine particles of such size, and the solubility is even decreased because of agglomeration or aggregation of the particles. In a preferred embodiment of the present invention, the preferable particle size of the active material can be in the range of 5 nm to 500 µm. In that range, the aggregation phenomenon is suppressed to the maximum, and the dissolution rate and solubility are maximized due to the increased specific surface area.

Hereinafter, the present invention is described in detail.

The present invention provides a pharmaceutical composition comprising the compound represented by formula 1 or formula 2 below, a pharmaceutically acceptable salt thereof, a prodrug thereof, a solvate thereof or an isomer thereof as an active ingredient for preventing or ameliorating any one or more side effects related to anticancer drug treatment selected from the group consisting of fatigue, cachexia, pain, cognitive decline, and hematopoietic stem cell reduction:

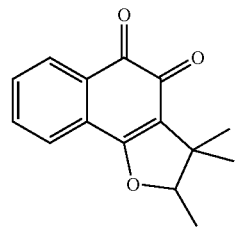

[Formula 1]

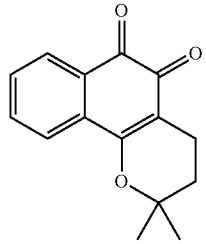

[Formula 2]

The composition above characteristically reduces the expression of inflammatory cytokines, particularly reduces the expression of inflammatory cytokines in the hypothalamus, blood, and bone marrow. Herein the cytokines are selected from the group consisting of TNF-α, IL-1B, IL-6, and IL-17.

The composition above characteristically suppresses the expression of intramuscular genes such as MAFbx, MuRF1 and Bnip3, arrests hematopoietic stem cells in the resting state, and prevents or improves hematopoietic stem cell reduction. The hematopoietic stem cells above are characteristically either long-term hematopoietic stem cells (HSCLT) or short-term hematopoietic stem cells (HSCST).

The cancer is preferably selected from the group consisting of liver cancer, stomach cancer, colon cancer, breast cancer, lung cancer, non-small cell lung cancer, bone cancer, pancreatic cancer, skin cancer, head or neck cancer, skin or intraocular melanoma, cervical cancer, ovarian cancer, colorectal cancer, small intestine cancer, rectal cancer, anal cancer, fallopian tube carcinoma, endometrial carcinoma, cervical carcinoma, vaginal carcinoma, vulvar carcinoma, Hodgkin's disease, esophageal cancer, small bowel cancer, lymphoma, bladder cancer, gallbladder cancer, endocrine cancer, thyroid cancer, papillary cancer, adrenal cancer, soft tissue sarcoma, urethral cancer, penile cancer, prostate cancer, chronic or acute leukemia, lymphocytic lymphoma, bladder cancer, kidney or ureter cancer, kidney cell carcinoma, kidney pelvic carcinoma, central nervous system (CNS) tumor, primary CNS lymphoma. spinal cord tumor, brainstem glioma and pituitary adenoma.

For the anticancer drug treatment above, it is preferable to administer the anticancer drugs alone or in combination with two or more anticancer drugs. In the case of the co-treatment, at least two of those anticancer drugs can be administered at different times from each other.

The anticancer drug above can be the conventional anticancer drug or the targeted anticancer drug that attacks only target cancer cells by a cancer specific molecular targeting (growth and metastasis of cancer by specific molecules involved in cancer growth and carcinogenesis), but not always limited thereto.

The conventional anticancer drug above is one or more drugs selected from the group consisting of adriamycin (ADR), cyclophisphamide (CYP), paclitaxel (PTX), docetaxel, gemcitabine (GEM), cisplatin, mitomycin-C, daunomycin, doxorubicin, daunorubicin, epirubicin, idarubicin, etoposide, teniposide, *vinca* alkaloid, vincristine, vinblastin, and 5-fluorouracil.

The targeted anticancer drug above is exemplified by signal transduction pathway inhibitors such as tyrosine kinase antagonist, Imatinib/Glivec, Transtuzumab/Herceptin, Cetuximab/Erbitux, Gefitinib/Iressa and Erlotinib/Taceva; and angiogenesis inhibitors and VEGF (vascular endothelial growth factor inhibitors such as Bevacizumab/Avsatine, Sunitinib/Sutent and Sorafenib/Nexavar (National Cancer Information Center, 2015).

The anticancer target therapy has the advantage of treating only cancer cells specifically but still has an issue of side effects accompanied by drugs (bone marrow dysfunction, fatigue, incompetence, nausea and vomiting, stomatitis and diarrhea, hemorrhagic cystitis. hair loss, nervous system side effects, and liver dysfunction) even though the incidence rate is lower than chemotherapy. One of tyrosine kinase inhibitors, Gleevec causes side effects such as nausea, vomiting, edema, muscle spasms, diarrhea, gastrointestinal and central nervous system bleeding, musculoskeletal pain, spots, headache, fatigue, arthralgia, weight gain, fever and abdominal pain in about 10% of total patients, and Herceptin causes heart failure in about 22% of patients. Erbitux accompanies such side effects as acne rash on the face, chest, back and scalp, fever, chills, nausea, diarrhea, immediate airway obstruction, urticaria, hypotensive symptoms, conjunctivitis, dyspnea, leukopenia, and hair loss. Iressa causes diarrhea, redness, acne, skin dryness, nausea, vomiting, itching, anorexia and asthenia in about 5% of patients. Taceva accompanies redness, diarrhea, anorexia, fatigue, nausea, vomiting, infection, stomatitis, itching, dry skin, conjunctivitis and abdominal pain in about 10% of patients. In the meantime, Avsatine, one of angiogenesis inhibitors, causes gastrointestinal perforation, hemorrhage, thrombosis, hypertension, and proteinuria. Sutent causes such side effects as characteristic hand syndrome and skin rash (National Cancer Institute, 2016; National Cancer Information Center, 2015; Babar et al. 2014; Liu and Kurzrock. 2014).

The present invention also provides a method for preventing or ameliorating any one or more side effects related to anticancer drug treatment selected from the group consisting of fatigue, cachexia, pain, cognitive decline, and hematopoietic stem cell reduction, which comprises the step of administering the compound represented by formula 1 or formula 2, a pharmaceutically acceptable salt thereof, a prodrug thereof, a solvate thereof or an isomer thereof to mammals.

In addition, the present invention provides a use of the compound represented by formula 1 or formula 2, a pharmaceutically acceptable salt thereof, a prodrug thereof, a solvate thereof or an isomer thereof for the preparation of a drug for preventing or ameliorating any one or more side effects related to anticancer drug treatment selected from the group consisting of fatigue, cachexia, pain, cognitive decline, and hematopoietic stem cell reduction.

In a preferred embodiment of the present invention, the present inventors established an animal model by intraperitoneally injecting one kind of an anticancer drug into mice once or more times or by intraperitoneally injecting several types of anticancer drugs at once or more times or at different concentrations. Dunnione and β-lapachone were orally administered everyday from 3 days prior to the anticancer drug administration. 2-4 days after the final administration of anticancer drug, FACS was performed to investigate the changes in blood, cytokines, Orexin-A, body weight, gastrocnemius muscle weight, quantitative and qualitative changes in bone marrow cells and hematopoietic stem cells/progenitor cells in each anticancer drug test animal. As a result, it was confirmed that dunnione and β-lapachone had an effect on fatigue, cachexia, pain, cognitive decline and hematopoietic stem cell reduction, the side effects related to anticancer drug treatment.

In each experimental animal model of anticancer drug, the changes of inflammatory cytokines in plasma were investigated. As a result, the levels of inflammatory cytokines (TNF-α, IL-1B, IL-6 and IL-17) in plasma of the anticancer drug treated group (treated with adriamycin or gemcitabine, or co-treated with adriamycin, cyclophosphamide and paclitaxel) were significantly increased compared with the normal group. In the meantime, the levels of inflammatory cytokines in plasma of the group treated with dunnione or β-lapachone were significantly reduced (see FIGS. 1, 3, and 13).

Considering the previous report saying that the reduction of orexin (neuronal hormone produced/secreted in the hypothalamus) is related to cancer-related fatigue in the course of anticancer drug treatment, the present inventors investigated the quantitative changes of orexin protein in the hypothalamus of the mouse co-treated with adriamycin, cyclophosphamide and paclitaxel. As a result, it was confirmed that the co-treatment of adriamycin, cyclophosphamide and paclitaxel reduced significantly the expression of orexin in the hypothalamus, compared with the normal group. It was also confirmed that the co-treatment of dunnione or β-lapachone was able to raise the expression of orexin significantly and thus back to the normal level (see FIGS. 4 and 14).

It is known that the increase of inflammatory cytokines in the hypothalamus causes the decrease of orexin neuron activity in the hypothalamus and causes cancer-related fatigue in the course of chemotherapy. So, the present inventors investigated the expression patterns of the inflammatory cytokines TNF-α and IL-1B in the mouse hypothalamus co-treated with adriamycin, cyclophosphamide and paclitaxel. As a result, it was confirmed that the co-treatment of adriamycin, cyclophosphamide and paclitaxel significantly increased the expressions of TNF-α and IL-1B at both RNA level and protein level in the mouse hypothalamus, compared with the normal group. It was also confirmed that the co-treatment of dunnione or β-lapachone suppressed significantly the decline of TNF-α and IL-1B at both RNA level and protein level so as to maintain them at normal levels (see FIGS. 5 and 15).

To investigate the effect of dunnione on cachexia caused in the course of anticancer drug treatment, the present inventors examined the effect of dunnione on muscle loss in a breast cancer animal model and other anticancer drug animal models. As a result, it was confirmed that the co-treatment of dunnione significantly restored the weight loss of gastrocnemius muscle induced by anticancer drug treatment. The inhibitory effect of dunnione on muscle loss was confirmed to be related to the regulation of the expressions of ubiquitin ligases (MAFbx and MuRF1) and autophagy gene (Binp3) directly involved in the muscle protein degradation (see FIGS. 6-8).

The present inventors investigated the effect of dunnione on the reduction of bone marrow hematopoietic stem cells induced by anticancer drug treatment. As a result, the number of total bone marrow cells was significantly reduced by the co-treatment of adriamycin, cyclophosphamide and paclitaxel. However, when dunnione was co-treated, the number of total bone marrow cells was significantly increased. The number of hematopoietic stem/progenitor cells was also reduced significantly by anticancer drug treatment, but it was recovered to the normal level when dunnione was co-treated with those anticancer drugs (see FIGS. 9 and 10).

It is known that the reduction of bone marrow hematopoietic stem cells is caused by the increase of TNF-α known as the inflammatory cytokine secreted by macrophages. So, the expressions of TNF-α and F4/80 (macrophage marker) in the femoral tissues obtained from the animal model co-treated with adriamycin, cyclophosphamide and paclitaxel were investigated by immunohistochemical staining. As a result, the expressions of TNF-α and F4/80 were significantly increased overall in the bone by the co-treatment of adriamycin, cyclophosphamide and paclitaxel, compared with the normal group. However, in the group treated with dunnione, the expressions above were significantly reduced (see FIGS. 11 and 12).

Therefore, it was confirmed that the naphthoquinone-based compounds dunnione and β-lapachone of the present invention were able to reduce the generation of inflammatory cytokines up-regulated by anticancer drug treatment, inhibit orexin reduction, and prevent cognitive decline and hematopoietic stem cell reduction. So, the naphthoquinone-based compounds of the present invention, pharmaceutically acceptable salts thereof, prodrugs thereof, solvates thereof or isomers thereof can be effectively used as an active ingredient of a pharmaceutical composition for preventing or ameliorating any one or more side effects related to anticancer drug treatment selected from the group consisting of fatigue, cachexia, pain, cognitive decline, and hematopoietic stem cell reduction.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Synthesis of β-Lapachone

Since β-lapachone is obtained from lapacho trees in a relatively small amount, but lapachol, a raw material of β-lapachone synthesis, is obtained from lapacho trees in a fairly large amount. So, a method for synthesizing β-lapachone using lapachol was developed a long time ago. That is, if lapachol and sulfuric acid are mixed together and vigorously stirred at room temperature, β-lapachone can be obtained with a relatively high yield.

In a preferred embodiment of the present invention, in order to obtain lapachol, 2-hydroxy-1,4-naphthoquinone (17.4 g, 0.10 M) was dissolved in DMSO (120 ml), to which LiH (0.88 g, 0.11 M) was slowly added. At this time, attention is needed because hydrogen is generated. The reaction solution was stirred. After confirming that hydrogen was not generated any more, the reaction solution was further stirred for 30 minutes. Then, prenyl bromide (1-Bromo-3-methyl-2-butene, 15.9 g, 0.10 M) and LiI (3.35 g, 0.025 M) were slowly added thereto. The reaction solution was heated until the temperature reached 45° C., followed by stirring vigorously for 12 hours. The reaction solution was cooled down to below 10° C. Then, ice (76 g) was added thereto and water (250 ml) was added next. The pH of the solution was maintained at 1 by adding concentrated hydrochloric acid (25 ml). EtOAc (200 ml) was added to the reaction solution, followed by stirring vigorously. As a result, a white solid insoluble in EtOAc was formed. The solid was filtered, and the EtOAc layer was separated. The water layer was extracted once again by using EtOAc (100 ml), which was then mixed with the organic layer that had already been extracted. The organic layer was washed with 5% $NaHCO_3$ (150 ml) and then concentrated. The concentrate was dissolved in $CH_2Cl_2$ (200 ml), to which 2N NaOH aqueous solution (70 ml) was added and the layer was separated by shaking vigorously. The $CH_2C_{12}$ layer was treated with 2N NaOH aqueous solution (70 ml×2), followed by separation two more times. The separated solutions were combined. Concentrated hydrochloric acid was used to regulate the acidity to be at least pH 2. The generated solid was separated by filtration to give lapachol. The obtained lapachol was recrystallized by using 75% EtOH. Sulfuric acid (80 ml) was added thereto and the mixture was stirred vigorously at room temperature for 10 minutes. The reaction was terminated by adding ice (200 g) The above process is expressed in the general structural formula as follows.

[Structural Formula]

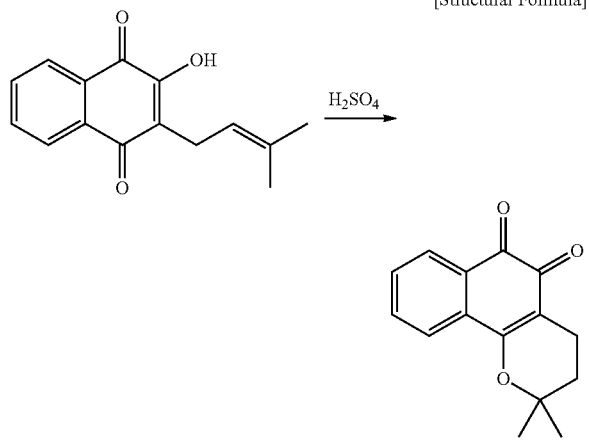

Next, $CH_2Cl_2$ (60 ml) was added to the reactant, which was stirred vigorously, leading to the separation of $CH_2Cl_2$ layer. The separated layer was washed with 5% $NaHCO_3$. The water layer was extracted once again by using $CH_2Cl_2$ (30 ml). The extracted water layer was washed with 5% $NaHCO_3$ and combined with the organic layer which had been extracted. The organic layer was dried over $MgSO_4$, followed by concentration. As a result, crude β-lapachone was obtained. The obtained crude β-lapachone was recrystallized by using isopropanol. As a result, purified β-lapachone (8.37 g) was obtained.

1H-NMR (CDCl3, δ): 8.05 (1H, dd, J=1, 8 Hz), 7.82 (1H, dd, J=1, 8 Hz), 7.64 (1H, dt, J=1, 8 Hz), 7.50 (1H, dt, J=1, 8 Hz), 2.57 (2H, t, J=6.5 Hz), 1.86 (2H, t, J=6.5 Hz) 1.47 (6H, s).

Example 2: Synthesis of Dunnione

The separated solid that were not dissolved in EtOAc in the process of obtaining lapachol in Example 1 was O-alylated 2-prenyloxy-1,4-maphthoquinone, unlike C-alylated lapachol. This solid was recrystallized once again by using EtOAc for purification. Then, the purified solid (3.65 g, 0.015 M) was dissolved in toluene, followed by reflux for 5 hours in order to induce claisen rearrangement. Toluene was concentrated by distillation under reduced pressure, and the resultant mixture was stirred vigorously at room temperature for 10 minutes while being mixed with sulfuric acid (15 ml) without further purification, and then the reaction was terminated by adding ice (100 g).

$CH_2Cl_2$ (50 ml) was added to the reactant, which was stirred vigorously, leading to the separation of $CH_2Cl_2$ layer. The separated layer was washed with 5% $NaHCO_3$. The water layer was extracted once again by using CH2Cl2 (20 ml). The extracted water layer was washed with 5% $NaHCO_3$ and combined with the organic layer which had been extracted.

The organic layer was dried over $MgSO_4$, followed by concentration. Then, pure dunnione was obtained (2.32 g) by silica gel chromatography. 1H-NMR (CDCl3, 6): 8.05 (1H, d, J=8 Hz), 7.64 (2H, d, J=8 Hz), 7.56 (1H, m), 4.67 (1H, q, J=7 Hz), 1.47 (3H, d, J=7 Hz), 1.45 (3H, s) 1.27 (3H, s).

Example 3: Synthesis of α-Dunnione

The 2-prenyloxy-1,4-maphthoquinone (4.8 g, 0.020 M) purified in Example 2 was dissolved in xylene, followed by reflux for 15 hours in order to induce claisen rearrangement at a higher temperature and for a longer time than the conditions of Example 1. In the course of the process, α-dunnione in the state of progressing to the cyclization reaction was obtained along with lapachol derivative wherein one of two methyl groups was rearranged. Then, xylene was concentrated by distillation under reduced pressure, followed by silica gel chromatography. As a result, pure α-dunnione was obtained (1.65 g).

1H-NMR (CDCl3, 6): 8.06 (1H, d, J=8 Hz), 7.64 (2H, m), 7.57 (1H, m), 3.21 (1H, q, J=7 Hz), 1.53 (3H, s), 1.51 (3H, s) 1.28 (3H, d, J=7 Hz).

Example 4: Preparation of Adriamycin Animal Model

In this invention, 11 weeks old C57BL/6 mice were used. All the mice used in the experiments of the invention were raised in an aseptic animal room at the temperature of 22~26° C. with the humidity of 55~60%. The mice were allowed to take general solid feed (SAMTACO Co., Ltd., Korea) and water freely. The mice were adapted for 1 week before the experiment. All the experiments were performed after obtaining approval from the clinical trial management committee in accordance with the laboratory animal care and ethics regulations of Wonkwang University. The mouse animal model of the present invention was treated with different anticancer drugs. Particularly, one kind of anticancer drug was administered intraperitoneally one time or more, or several kinds of anticancer drugs were administered once or more times or at different concentrations, leading to the establishment of the animal model of the invention. In the adriamycin-induced animal model, the mice were divided into 6 groups as follows: the control group administered with PBS (Control, mice), the group administered intraperitoneally with adriamycin (4 mg/kg/day) 3 times (ADR, 5 mice), the group administered orally with dunnione or β-lapachone from 3 days before the adriamycin treatment daily (20 mg/kg, 5 mice), and the group administered with dunnione or β-lapachone (20 mg/kg, 5 mice). 4 days after the final adriamycin treatment, analysis of the mice was performed.

Example 5: Preparation of Gemcitabine (500 mg/kg) Animal Model

In the gemcitabine (500 mg/kg) induced animal model, the mice were divided into 4 groups as follows: the control group administered with PBS (Control, 5 mice), the group administered intraperitoneally with gemcitabine (500 mg/kg/day) once (GEM, 5 mice), the group administered orally with dunnione from 3 days before the gemcitabine treatment daily (20 mg/kg, 5 mice), and the group administered with dunnione (20 mg/kg, mice). 2 days after the gemcitabine treatment, analysis of the mice was performed.

Example 6: Preparation of Animal Model Co-Treated with Adriamycin, Cyclophosphamide and Paclitaxel (3×ACP)

The present inventors established an animal model co-treated with three different anticancer drugs in this experiment. The anticancer drugs used herein were adriamycin (ADR), cyclophosphamide (CYP) and paclitaxel (PTX), which were indicated as ACP (tentative name). The concentration of each anticancer drug for the treatment to the mice was based on the single dose (indicated as 1× concentration)

that was clinically applied to cancer patients, and the basic information about the dose was obtained from National Comprehensive Cancer Network (NCCN). The concentrations of adriamycin, cyclophosphamide and paclitaxel at 3× were respectively 4.62 mg/kg, 46.2 mg/kg and 6.18 mg/kg, which were administered with one hour interval for the full absorption of each drug in the course of the anticancer drug treatment. In the ACP induced animal model, the mice were divided into 4 groups as follows: the control group administered with PBS (Control, 10 mice), the group administered intraperitoneally with 3×ACP once (3×ACP, 10 mice), the group administered orally with dunnione from 3 days before the 3×ACP treatment daily (20 mg/kg, 10 mice), and the group administered with dunnione (20 mg/kg, 10 mice). 2 days and 4 days after the ACP treatment, analysis of the mice was performed.

Example 7: Preparation of Animal Model Co-Treated with Adriamycin, Cyclophosphamide and Paclitaxel (3×, 6×ACP)

The present inventors established an animal model co-treated with three different anticancer drugs in this experiment. The anticancer drugs used herein were adriamycin (ADR), cyclophosphamide (CYP) and paclitaxel (PTX), which were indicated as ACP (tentative name). The concentration of each anticancer drug for the treatment to the mice was based on the single dose (indicated as 1× concentration) that was clinically applied to cancer patients, and the basic information about the dose was obtained from National Comprehensive Cancer Network (NCCN). The concentrations of adriamycin, cyclophosphamide and paclitaxel were respectively 4.62 mg/kg, 46.2 mg/kg and 6.18 mg/kg at 3×, and respectively 9.24 mg/kg, 92.4 mg/kg and 12.36 mg/kg at 6×, which were administered with one hour interval for the full absorption of each drug in the course of the anticancer drug treatment. In the ACP induced animal model, the mice were divided into 6 groups as follows: the control group administered with PBS (Control. 5 mice), the group administered intraperitoneally with 3×ACP once (3×ACP, 5 mice), the group administered orally with dunnione from 3 days before the 3×ACP treatment daily (20 mg/kg, 5 mice), the group administered intraperitoneally with 6×ACP once (6×ACP, 5 mice), the group administered orally with dunnione from 3 days before the 6×ACP treatment daily (20 mg/kg, 5 mice), and the group administered with dunnione (20 mg/kg, 5 mice). 3 days after the ACP treatment, analysis of the mice was performed.

Example 8: Preparation of Animal Model Co-Treated with Adriamycin, Cyclophosphamide and Paclitaxel (4×ACP)

The present inventors established an animal model co-treated with three different anticancer drugs in this experiment. The anticancer drugs used herein were adriamycin (ADR), cyclophosphamide (CYP) and paclitaxel (PTX), which were indicated as ACP. The concentration of each anticancer drug for the treatment to the mice was based on the single dose (indicated as 1× concentration) that was clinically applied to cancer patients, and the basic information about the dose was obtained from National Comprehensive Cancer Network (NCCN). The concentrations of adriamycin, cyclophosphamide and paclitaxel were respectively 1.54 mg/kg, 15.4 mg/kg and 2.06 mg/kg at IX, which were intraperitoneally administered at intervals of 2 days for 4 days. In the 4×ACP induced animal model, the mice were divided into 6 groups as follows: the control group administered with PBS (Control, 5 mice), the group administered intraperitoneally with 1×ACP daily for 4 days (4×ACP, 5 mice), the group administered orally with dunnione (80 mg/kg, 5 mice) or β-lapachone (20 mg/kg, 5 mice) from 3 days before the 4×ACP treatment daily, and the group administered with dunnione (80 mg/kg, 5 mice) or β-lapachone (20 mg/kg, 5 mice). 2 days after the ACP treatment, analysis of the mice was performed.

Example 9: Preparation of Cyclophosphamide (350 mg/kg) Induced Animal Model

In the cyclophosphamide induced animal model, the mice were divided into 4 groups as follows: the control group administered with PBS (Control, 5 mice), the group administered intraperitoneally with cyclophosphamide at the concentrations of 150 mg/kg and 200 mg/kg stepwise at three days intervals (total 350 mg/kg) (CYP, 5 mice), the group administered orally with dunnione (20 mg/kg, 5 mice) from 3 days before the cyclophosphamide treatment daily, and the group administered with dunnione (20 mg/kg, 5 mice). 48 hours after the cyclophosphamide treatment, analysis of the mice was performed.

Example 10: Preparation of Animal Model Co-Treated with Adriamycin, Cyclophosphamide and Paclitaxel (3×ACP) for the Analysis of Bone Marrow Hematopoietic Stem Cell Protective Effect In the 3×ACP induced animal model for the analysis of bone marrow hematopoietic stem cell protective effect, the mice were divided into 4 groups as follows: the control group administered with PBS (Control, 4 mice), the group administered intraperitoneally with 3×ACP once (3×ACP, 4 mice), the group administered orally with dunnione from 3 days before the 3×ACP treatment daily (20 mg/kg, 4 mice), and the group administered with dunnione (20 mg/kg, 4 mice). 2 days after the ACP treatment, analysis of the mice was performed.

Experimental Example 1: Regulatory Effect of Dunnione on Adriamycin Induced Inflammatory Cytokines Cytokines are involved in immune system and inflammation response and thus regulate various biological responses. Under the normal condition, cytokines are strictly regulated, but any in vivo changes including inflammation can cause excessive production and secretion of cytokines, which can mediate or exacerbate various diseases and disorders. In particular, the excessive production and secretion of TNF-α, IL-1B, IL-6 or IL-17 have been confirmed to be closely involved in not only cancer itself but also cancer-related fatigue, cachexia, pain, cognitive decline and hematopoietic stem cell reduction. Therefore, the present inventors analyzed the level of cytokines in plasma of the animal models established herein.

Particularly, plasma was isolated from the adriamycin animal model prepared by the same manner as described in Example 4, and the inflammatory cytokines TNF-α (R & D Systems, MTA00B), IL-1β (R & D Systems, MLB00C), IL-6 (R&D Systems, M6000B) and IL-17 (R&D Systems, M1700) were analyzed by ELISA (enzyme-linked immunosorbent assay).

Figure 1:
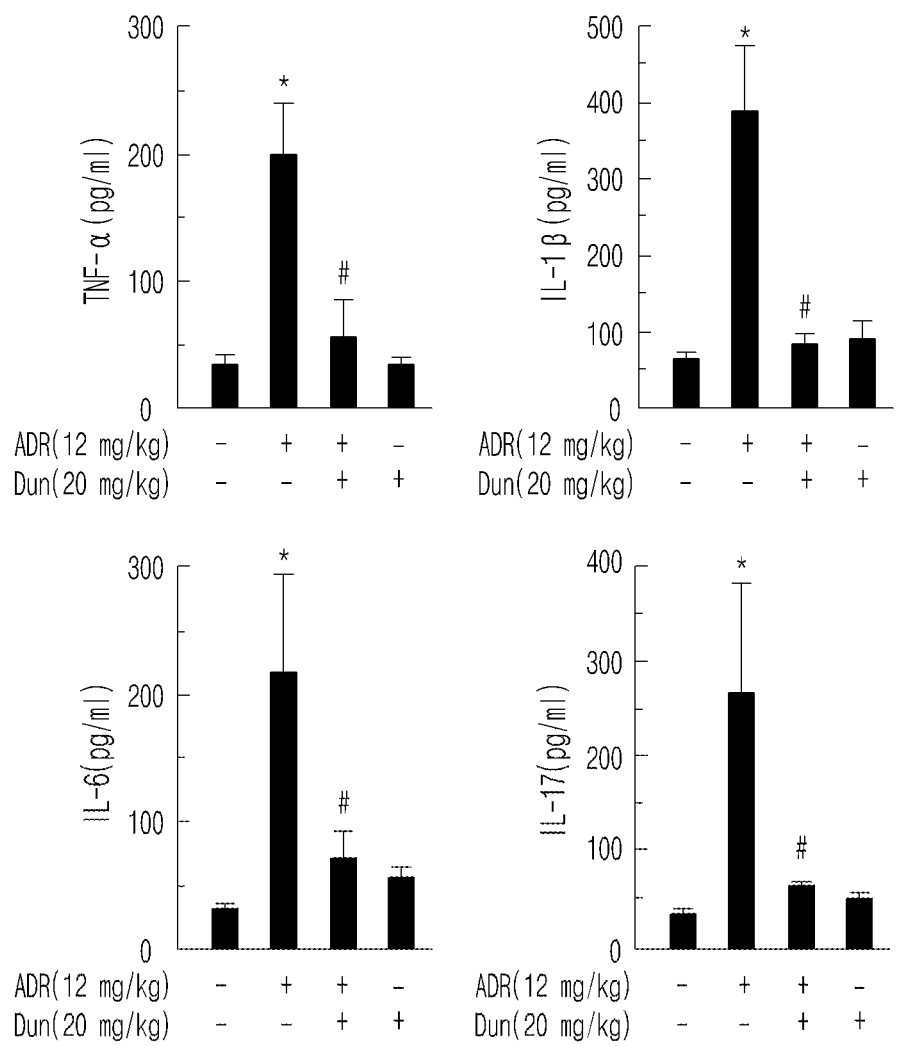
FIG. 1 is a diagram illustrating the regulatory effect of dunnione on inflammatory cytokines (TNF-α, IL-1β, IL-6, and IL-17) in plasma induced by adriamycin.

As a result, as shown in FIG. 1, it was confirmed that the amount of inflammatory cytokines in plasma of the adriamycin treated group was significantly increased, compared with the normal group. In the meantime, the level of those cytokines was significantly reduced in the group co-treated with dunnione.

Experimental Example 2: Regulatory Effect of Dunnione on Gemcitabine Induced Inflammatory Cytokines Plasma was isolated from the gemcitabine animal model prepared by the same manner as described in Example 5, and the inflammatory cytokines TNF-α, IL-1B, IL-6 and IL-17 were analyzed by ELISA.

As a result, as shown in FIG. 2, it was confirmed that the amount of inflammatory cytokines in plasma of the gemcitabine treated group was significantly increased, compared with the normal group. In the meantime, the level of those cytokines was significantly reduced in the group co-treated with dunnione.

Experimental Example 3: Regulatory Effect of Dunnione on Inflammatory Cytokines Induced by Adriamycin, Cyclophosphamide and Paclitaxel Plasma was isolated from the 3× and 6×ACP animal model prepared by the same manner as described in Example 7, and the inflammatory cytokines TNF-α, IL-1B, IL-6 and IL-17 were analyzed by ELISA.

As a result, as shown in FIG. 3, as the ACP concentration increased, the level of those cytokines was also increased, compared with the normal group. In the meantime, in the group co-treated with dunnione, the level of those cytokines was significantly inhibited not only in the group treated with 3×ACP but also in the group treated with 6×ACP.

Experimental Example 4: Regulatory Effect of Dunnione on Orexin Induced by Adriamycin, Cyclophosphamide and Paclitaxel To analyze orexin protein in the 4×ACP animal model prepared by the same manner as described in Example 8, the hypothalamus of the mouse was extracted, followed by the preparation of a homogenate. ELISA was performed to investigate the changes of orexin (MyBioSource, MBS2505504) according to the concentration of dunnione.

As a result, as shown in FIG. 4, orexin was significantly reduced in the hypothalamus by the treatment of 4×ACP, compared with the normal group. In the group treated with dunnione at the concentration of 80 mg/kg, the orexin reduction was recovered significantly almost to the same level of the control group.

Experimental Example 5: Regulatory Effect of Dunnione on Brain Inflammatory Response Induced by Adriamycin, Cyclophosphamide and Paclitaxel The hypothalamus of the mouse was extracted from the 4×ACP animal model prepared by the same manner as described in Example 8, from which RNA and protein were extracted. Then, RT-PCR and ELISA were performed to investigate the expressions of the inflammatory cytokines TNF-α and IL-1B in brain tissues.

As a result, as shown in FIG. 5, the expressions of TNF-α and IL-1B were significantly increased at RNA level (left) and at protein level (right) in the hypothalamus by the treatment of 4×ACP, compared with the control group. In the group treated with dunnione at the concentration of 80 mg/kg, the up-regulations of TNF-α and IL-1B at RNA level and at protein level induced by the treatment of 4×ACP were significantly suppressed in the hypothalamus.

Experimental Example 6: Regulatory Effect of Dunnione on Muscle Loss Induced by Adriamycin, Cyclophosphamide and Paclitaxel To investigate the regulatory effect of dunnione on muscle loss in the 3×ACP animal models prepared by the same manner as described in Example 6, the changes of body weight and gastrocnemius muscle weight were measured after the drug treatment.

As a result, as shown in FIG. 6, the weight loss induced by 3×ACP was significantly restored by dunnione. The reduction of gastrocnemius muscle weight and gastrocnemius muscle weight change caused by 3×ACP was also significantly restored by the treatment of dunnione.

Experimental Example 8: Regulatory Effect of Dunnione on Muscle Loss Induced by Cyclophosphamide In the cyclophosphamide (150 mg/kg+200 mg/kg) induced animal model prepared by the same manner as described in Example 9, the changes of body weight and gastrocnemius muscle weight were measured after the drug treatment in order to investigate the regulatory effect of dunnione on muscle loss.

As a result, as shown in FIG. 7, the weight loss induced by cyclophosphamide was significantly restored by dunnione. The reduction of gastrocnemius muscle weight and gastrocnemius muscle weight change caused by cyclophosphamide was also significantly restored by the treatment of dunnione.

Experimental Example 9: Regulatory Effect of Dunnione on Cyclophosphamide Induced Muscle Loss Related Gene Expression In the cyclophosphamide (350 mg/kg) induced animal model prepared by the same manner as described in Example 9, the regulatory effect of dunnione on the expressions of ubiquitin ligases (MAFbx and MuRF1) and autophagy gene (Bnip3) directly related to protein degradation in muscle.

As a result, as shown in FIG. 8, the expressions of MAFbx, MuRF1 and Bnip3 mRNAs were significantly increased by cyclophosphamide but the increased expressions were significantly reduced by the treatment of dunnione.

Experimental Example 10: Inhibitory Effect of Dunnione on Bone Marrow Hematopoietic Stem Cell Reduction Induced by Co-Treatment of Adriamycin, Cyclophosphamide and Paclitaxel (3×ACP)

The femur and tibia were extracted from the animal model prepared by the same manner as described in Example 10, from which bone tissues were obtained by completely eliminating soft tissues. To separate the cells in the bone, HEPES buffer was pushed in by using a syringe to obtain bone marrow cells. To confirm the bone marrow cells such as hematopoietic stem cells (HSC) and multipotent progenitor cells (MPP), the cells were reacted with the antibodies corresponding to each cell marker; the lineage positive cell (Lin+) antibodies (CD3, B220, CD11b, TER-119, and Ly-6G); and the lineage negative cell (Lin−) antibodies (Sca-1, c-Kit, CD150, CD48, and Flk2), followed by flow cytometry (Pietras et al. 2015; Schulte et al. 2015; Wognum. 2015).

As a result, as shown in FIG. 9 presenting the results of flow cytometry for the quantitative analysis of bone marrow hematopoietic cells, the region where lineage negative cells were distributed was gated. Then, the cells double positive to the stem cell marker Sca-1 and c-Kit (LSK; Lin-Sca-1+ c-Kit+) were confirmed therein. Next, hematopoietic stem cells and multipotent progenitor cells were separated and analyzed, leading to the analysis of multipotent progenitor cell-4 (MPP4) and hematopoietic stem cell/progenitor cell (HSPC). With the hematopoietic stem cell/progenitor cell group, long-term hematopoietic stem cells (HSCLT), short-term hematopoietic stem cells (HSCST), and multipotent progenitor cell-2 and-3 (MPP2 and MPP3) were analyzed. In FIG. 9, the results of flow cytometry analyzed for each group are presented. The percentage of each cell group and the cell number of each group are also presented.

In FIG. 10, the number of each cell line obtained from flow cytometry is presented in a bar graph for the quantitative comparison. The total bone marrow cells were reduced at least 65% by the treatment of the anticancer drugs adriamycin, cyclophosphamide and paclitaxel. However, when dunnione was co-treated with them, the total number was raised at least three times the number of the group treated with the anticancer drugs. The number of hematopoietic stem cell/progenitor cell was reduced at least 75% by the treatment of adriamycin, cyclophosphamide and paclitaxel, but was raised again by the treatment of dunnione as much as three times the number before. In the meantime, the distribution of hematopoietic cells was also investigated. As a result, the treatment of anticancer drugs adriamycin, cyclophosphamide and paclitaxel reduced the numbers of long-term hematopoietic stem cells (HSCLT) and short-term hematopoietic stem cells (HSCST) respectively 55% and 90% by the number of the control group. However, when dunnione was co-treated with the anticancer drugs adriamycin, cyclophosphamide and paclitaxel, the numbers of long-term hematopoietic stem cells and short-term hematopoietic stem cells were increased at least 2 times and 8 times the group treated with the anticancer drugs. The group treated with dunnione alone displayed the similar cell distribution to the control group.

Experimental Example 11: Effect of Dunnione on the Expression of TNF-α in Bone Induced by Co-Treatment of Adriamycin, Cyclophosphamide and Paclitaxel TNF-α, one of the inflammatory cytokines, is known to suppress the maintenance of hematopoietic stem cells. So, to investigate the expression of TNF-α in the bone, the femur was isolated from the 4×ACP animal model prepared by the same manner as described in Example 8, followed by immunohistostaining using TNF-α antibody (Santa Cruz, USA, sc-1348).

As a result, as shown in FIG. 11, the expression of TNF-α (red-brown) was significantly increased overall in the bone by the treatment of 4×ACP, compared with the control group. However, the up-regulation of TNF-α in the bone caused by the treatment of 4×ACP was significantly suppressed in the group treated with dunnione at the concentration of 80 mg/kg.

Experimental Example 12: Effect of Dunnione on the Inflow of Macrophages into the Femur Induced by Co-Treatment of Adriamycin, Cyclophosphamide and Paclitaxel The expression of TNF-α, which is known to inhibit the maintenance and activation of hematopoietic stem cells, is secreted mainly in macrophages. So, to investigate the changes of macrophages in the bone, the femur was isolated from the 4×ACP animal model prepared by the same manner as described in Example 8, followed by immunohistostaining using F4/80 antibody (Santa Cruz, USA, sc-377009) known as a macrophage marker.

As a result, as shown in FIG. 12, the number of F4/80 positive cells (marked by arrow) in the bone was significantly increased by the treatment of 4×ACP, compared with the control group. In the meantime, the increased F4/80 positive cells induced by the treatment of 4×ACP were significantly reduced in the group treated with dunnione at the concentration of 80 mg/kg.

Experimental Example 13: RegulatoryeEffect of β-Lapachone on Adriamycin Induced Inflammatory Cytokines To investigate the regulatory effect of β-lapachone on adriamycin induced inflammatory cytokines, plasma was isolated from the adriamycin animal model prepared by the same manner as described in Example 4, and the inflammatory cytokines TNF-α, IL-1B, IL-6 and IL-17 were analyzed by ELISA.

As a result, as shown in FIG. 13, it was confirmed that the amount of inflammatory cytokines in plasma of the adriamycin treated group was significantly increased, compared with the control group. In the meantime, the level of those cytokines was significantly reduced in the group co-treated with β-lapachone.

Experimental Example 14: Regulatory Effect of β-Lapachone on Orexin Induced by Adriamycin, Cyclophosphamide and Paclitaxel To analyze orexin protein in the 4×ACP animal model prepared by the same manner as described in Example 8, the hypothalamus of the mouse was extracted, followed by the preparation of a homogenate. Orexin (MyBioSource, MBS2505504) was analyzed by ELISA to investigate the regulatory effect of β-lapachone on orexin.

As a result, as shown in FIG. 14, orexin was significantly reduced in the hypothalamus by the treatment of 4×ACP, compared with the control group. In the group treated with β-lapachone, the orexin reduction was significantly restored.

Experimental Example 15: Regulatory Effect of β-Lapachone on Brain Inflammatory Response Induced by Adriamycin, Cyclophosphamide and Paclitaxel A homogenate was prepared with the mouse hypothalamus extracted from the 4×ACP animal model prepared by the same manner as described in Example 8. Then, the expressions of the inflammatory cytokines TNF-α and IL-1B in the brain tissue were analyzed by ELISA.

IL-1β were significantly increased in the hypothalamus by the treatment of 4×ACP, compared with the control group. In the group treated with β-lapachone, the up-regulations of TNF-α and IL-1β induced by the treatment of 4×ACP were significantly suppressed in the hypothalamus.

From the results above, it was confirmed that the naphthoquinone-based compounds dunnione and β-lapachone were excellent in ameliorating cancer-related fatigue, suppressing cachexia, relieving pain, improving cognitive decline and maintaining the number of hematopoietic stem cells by reducing the secretion and generation of inflammatory cytokines which had increased by the treatment of anticancer drugs.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for ameliorating cancer-related fatigue and/or cachexia of a subject,
   said method comprising administering an effective amount of the compound of Formula 1 below or a pharmaceutically acceptable salt thereof to the subject,
   wherein the subject suffers from cancer and receives a chemo-therapy using an anticancer drug,
   wherein the anticancer drug is a combination of adriamycin, cyclophosphamide, and paclitaxel (ACP);
   wherein the compound of formula 1 or the pharmaceutically acceptable salt thereof reduces expression of inflammatory cytokines in hypothalamus, blood, and bone marrow;
   wherein the inflammatory cytokines are one or more cytokines selected from the group consisting of TNF-α, IL-1β, IL-6, and IL-17;

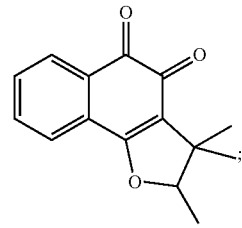

[Formula 1]

and
   wherein the effective amount of the compound of formula 1 or the pharmaceutically acceptable salt thereof is 20 mg/kg to 80 mg/kg.

2. The method according to claim 1, wherein the subject has an increased level of expressions of MAFbx, MuRF1 and Bnip3 genes in muscle.

3. The method according to claim 1, wherein the subject has a reduced level of hematopoietic stem cells.

4. The method according to claim 3, wherein the hematopoietic stem cells are long-term hematopoietic stem cells (HSCLT) or short-term hematopoietic stem cells ($HSC^{ST}$).

5. The method of claim 1, wherein the dosage of the compound of formula 1 or the pharmaceutically acceptable salt thereof is 20 mg/kg, 40 mg/kg, 60 mg/kg, or 80 mg/kg.

* * * * *